(12) United States Patent
Garcia Castellano

(10) Patent No.: US 10,172,857 B2
(45) Date of Patent: Jan. 8, 2019

(54) BOOSTING THE EFFECT OF METHOTREXATE THROUGH THE COMBINED USE WITH LIPOPHILIC STATINS

(71) Applicant: Dalana3, S.L., Las Palmas de Gran Canaria (ES)

(72) Inventor: Jose Manuel Garcia Castellano, La Palmas de Gran Canaria (ES)

(73) Assignee: DALANA3, S.L. (ES)

( * ) Notice: Subject to any disclaimer, the term of this patent is extended or adjusted under 35 U.S.C. 154(b) by 0 days.

(21) Appl. No.: 14/909,210

(22) PCT Filed: Aug. 1, 2014

(86) PCT No.: PCT/ES2014/070628
§ 371 (c)(1),
(2) Date: Feb. 1, 2016

(87) PCT Pub. No.: WO2015/015039
PCT Pub. Date: Feb. 5, 2015

(65) Prior Publication Data
US 2016/0175310 A1    Jun. 23, 2016

(30) Foreign Application Priority Data
Aug. 2, 2013 (ES) .................................. 201331207

(51) Int. Cl.
| | | |
|---|---|---|
| A61K 31/519 | (2006.01) | |
| A61K 31/366 | (2006.01) | |
| A61K 31/40 | (2006.01) | |
| A61K 31/404 | (2006.01) | |
| A61K 31/517 | (2006.01) | |
| A61K 45/06 | (2006.01) | |
| A61K 9/00 | (2006.01) | |

(52) U.S. Cl.
CPC .......... A61K 31/519 (2013.01); A61K 9/0014 (2013.01); A61K 9/0019 (2013.01); A61K 9/0031 (2013.01); A61K 9/0053 (2013.01); A61K 31/366 (2013.01); A61K 31/40 (2013.01); A61K 31/404 (2013.01); A61K 31/517 (2013.01); A61K 45/06 (2013.01)

(58) Field of Classification Search
CPC .... A61K 31/366; A61K 31/40; A61K 31/404; A61K 31/517; A61K 31/519; A61K 9/0053; A61K 9/0031; A61K 9/0019; A61K 9/0014; A61K 45/06
USPC ......................................................... 514/249
See application file for complete search history.

(56) References Cited

U.S. PATENT DOCUMENTS

| | | | | |
|---|---|---|---|---|
| 4,658,957 A * | 4/1987 | Guth .................... | A61J 7/0069 | 206/365 |
| 2001/0013643 A1 | 8/2001 | Nakanishi et al. | | |
| 2004/0013643 A1 | 1/2004 | Mach | | |
| 2007/0003636 A1* | 1/2007 | Mach ..................... | A61K 45/06 | 424/649 |
| 2010/0093636 A1* | 4/2010 | Schultz .................. | A61K 45/06 | 514/1.1 |
| 2012/0053196 A1* | 3/2012 | Jirstrom ............... | A61K 31/366 | 514/277 |
| 2013/0064812 A1* | 3/2013 | Gallatin ............. | A61K 39/3955 | 424/133.1 |
| 2013/0116215 A1* | 5/2013 | Coma .................. | A61K 31/165 | 514/108 |

OTHER PUBLICATIONS

Schweitzer et al., "Dihydrofolate reductase as a therapeutic target", 1990, The FASEB Journal, 4(8), pp. 2441-2452.*
Bruce N. Cronstein, "Low-Dose Methotrexate: A Mainstay in the Treatment of Rheumatoid Arthritis", 2005, Pharmacological Reviews, 57(2), pp. 163-172.*
Kim et al., "Comparison of Clinical Outcomes of Hydrophilic and Lipophilic Statins in Patients with Acute Myocardial Infarction", 2011, Korean Journal of Internal Medicine, 26(3), pp. 294-303.*
Izdebska et al., "Preliminary Studies Evaluating Cytotoxic Effect of Combined Treatment With Methotrexate and Simvastatin on Green Monkey Kidney Cells", 2014, Drug Research, 71(3), pp. 515-520.*
Abud-Mendoza C et al., "Therapy with Statins in Patients with Refractory Rheumatic Diseases: A Preliminary Study", Lupus (2003) 12, pp. 607-611, www.lupus-journal.com.
Kabel et al.; "Effect of atorvastatin and methotrexate on solid Ehrlich tumor"; Molecular and cellular pharmacology; European Journal of Pharmacology; 2013; pp. 47-53; vol. 713; Elsevier.
El-Barbary et al.; "Effect of Atorvastatin on Inflammation and Modification of Vascular Risk Factors in Rheumatoid Arthritis"; The Journal of Rheumatology; 2011; pp. 229-235; vol. 38, issue 2.
Abud-Mendoza et al.; "Therapy with statins in patients with refractory rheumatic diseases: a preliminary study"; Lupus; 2003; pp. 607-611; vol. 12; Arnold.
Ciminello Lauren et al.; "Statin Use Improves Overall Survival and Time to Treatment Failure in Patients with Primary CNS Lymphoma"; Database Biosis (Online) Biosciences Information Service, Philadelphia, PA, Nov. 20, 2009.

* cited by examiner

Primary Examiner — My-Chau T. Tran
(74) Attorney, Agent, or Firm — Hayes Soloway PC

(57) ABSTRACT

The invention relates to the use of an inhibitor of the dihydrofolate reductase enzyme selected from the group that consists of methotrexate, trimetrexate and pemetrexed; or a pharmaceutically acceptable salt thereof, for the preparation of a drug for the treatment or prevention of recurrences of a disease selected from the group that consists of cancer, psoriasis, psoriatic arthritis, juvenile polyarticular arthritis, rheumatoid arthritis, Crohn's disease, polymyositis, dermatomyositis and sarcoidosis, wherein said treatment or prevention includes administering to a patient, simultaneously, separately or sequentially, a lipophilic statin and the inhibitor of the dihydrofolate reductase enzyme. The invention also relates to a pharmaceutical composition which includes the inhibitor of the dihydrofolate reductase enzyme and the lipophilic statin together with pharmaceutically acceptable carriers and/or vehicles.

4 Claims, 22 Drawing Sheets

|  | A | B | C |
|---|---|---|---|
| Control | 100.00 | 58.73 | 41.27 |
| 10 nM | 104.52 | 56.46 | 48.06 |
| 20 nM | 81.16 | 52.31 | 28.85 |
| 30 nM | 47.62 | 33.30 | 14.32 |
| 40 nM | 32.43 | 24.66 | 7.76 |
| 50 nM | 24.12 | 17.50 | 6.63 |
| 60 nM | 16.49 | 12.14 | 4.35 |
| 80 nM | 11.07 | 6.99 | 4.08 |
| 100 nM | 8.06 | 5.92 | 2.14 |

BOOSTING THE EFFECT OF METHOTREXATE THROUGH THE COMBINED USE WITH LIPOPHILIC STATINS

The present invention relates to the field of clinical medicine, particularly to the field of oncology and autoimmune diseases such as psoriasis and rheumatoid arthritis. Specifically, the invention provides an improved therapy for these diseases through the combination of methotrexate with lipophilic statins.

STATE OF THE ART

Methotrexate ((2S)-2-[(4-{[(2,4-diaminopteridin-6-yl)methyl](methyl)amino}benzoyl)amino]pentanedioic acid, CAS number 59-05-2, Formula I abbreviated as MTX) is an antimetabolite that has anti-proliferative and anti-inflammatory activity by competitively inhibiting the dihydrofolate reductase enzyme (DHFR), an enzyme that regulates the intracellular folate available for the synthesis of nucleic acids in the S phase of the cell cycle and that prevents the conversion of homocysteine to methionine during protein synthesis.

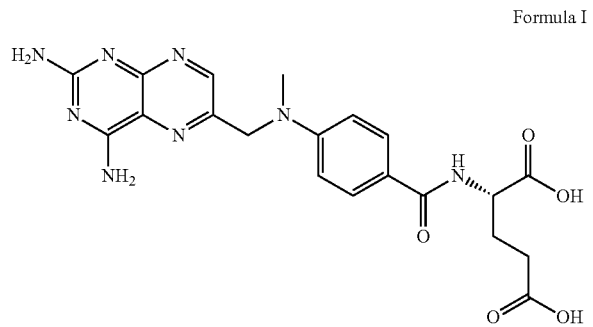 [SMILES: CN(Cc1cnc2nc(N)nc(N)c2n1)c1ccc(C(=O)N[C@@H](CCC(=O)O)C(=O)O)cc1]

Formula I

MTX is used as in first line chemotherapy for the treatment of certain neoplastic diseases such as osteosarcoma. It is administered for a number of neoplastic disorders in highly elevated doses (3 to 12 g/m$^2$ of patient surface area), in patients with normal kidney function and it is administered with hyperhydration (3 l/m$^2$ of patient surface area) and alkalinisation. It is also used for the treatment of some inflammatory diseases including psoriatic arthritis and rheumatoid arthritis.

However, it is a drug that, on occasion, produces significant and severe adverse side effects that determines an elevated morbi-mortality in patients that use the drug. In some cases even forces the premature interruption of chemotherapy in a third of patients despite inclusion of a suitable rescue with folinic acid.

Myelosuppression, mucositis and neurotoxicity with acute or chronic encephalopathy have been described in patients treated with MTX. Acute encephalopathy generally develops in 3%-15% of patients within the first 5 to 14 days after the beginning of the treatment and it can include headache, nausea, vomiting, lethargy, alteration of the mental state, blurred vision, aphasia, hemiparesis and convulsions. In these cases the majority of the patients restart their treatment with MTX without permanent neurological consequences, although 10%-56% can experiment recurrences with reexposition. Chronic encephalopathy may also occur that develops slowly, it can progress and it can permanently damage neurological functioning.

The administration of MTX in high doses is of vital importance in children affected by osteosarcomas. In these cases, the delay in MTX elimination and prolonged exposure to this drug can lead to significant toxicity, mainly acute kidney failure due to a secondary renal obstruction from the deposit of crystals of MTX and its metabolites (17-hydroxymethotrexate) in the renal tubules or even due to the pharmaceutical's direct toxicity to these tubules.

These problems therefore require therapies to be found that are able to decrease the harmful side effects of treatment with MTX while maintaining or improving its anti-inflammatory, immunomodulatory and anti-tumour activity.

EXPLANATION OF THE INVENTION

The inventor has found that the combined use of a lipophilic statin and an inhibitor of the dihydrofolate reductase (DHFR) enzyme, such as for example methotrexate (MTX), produces a synergistic effect in the treatment of the cancer and autoimmune diseases for which treatment with these DHFR inhibiting drugs are indicated. As is shown in the example provided below, the use on a lipophilic statin in combination therapy with MTX strengthens MTX's anti-tumour effect, allowing the MTX dose to be decreased without affecting the treatment's efficacy. This combination therapy provides enormous benefits to patients that suffer a disease where the indicated treatment is the administration of a DHFR inhibitor, such as, for example, patients with cancer or some autoimmune diseases, because, as a consequence of their exposure to lower doses of the DHFR inhibitor, these patients have fewer side effects without affecting the treatment's efficacy.

Therefore, a first aspect of the invention provides a DHFR enzyme inhibitor selected from the group consisting of methotrexate, trimetrexate and pemetrexed; or a pharmaceutically acceptable salt thereof, for its use in the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis, wherein said treatment comprises administering simultaneously, separately or sequentially to a subject a lipophilic statin and an inhibitor of the dihydrofolate reductase enzyme selected from the group that consists of methotrexate, trimetrexate and pemetrexed; or a pharmaceutically acceptable salt thereof. This aspect can be reformulated as the use of an inhibitor of the dihydrofolate reductase enzyme selected from the group that consists of methotrexate, trimetrexate and pemetrexed; or a pharmaceutically acceptable salt thereof, for the preparation of a medicament for the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis, wherein said treatment comprises administering simultaneously, separately or sequentially to a subject a lipophilic statin and an inhibitor of the DHFR enzyme. The present invention also provides a method for the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis, in a patient in need thereof it, wherein said treatment method comprises administering simultaneously, separately or sequentially to a subject a lipophilic statin and an inhibitor of the dihydrofolate reductase enzyme selected from the group that consists of methotrexate, trimetrexate and pemetrexed; or a pharmaceutically acceptable salt thereof.

The lipophilic statins are those that are slightly soluble in water. In a specific embodiment of the invention the lipophilic statin that is used in therapy combined with MTX is simvastatin (CAS number: 79902-63-9, Formula II) or a pharmaceutical salt thereof. In another specific embodiment, the lipophilic statin is atorvastatin (CAS number: 134523-00-5, Formula V) or a pharmaceutical salt thereof. In another specific embodiment, the lipophilic statin is fluvastatin (CAS number: 93957-54-1, Formula IV) or a pharmaceutical salt thereof. In another specific embodiment, the lipophilic statin is lovastatin (CAS number: 75330-75-5, Formula III).

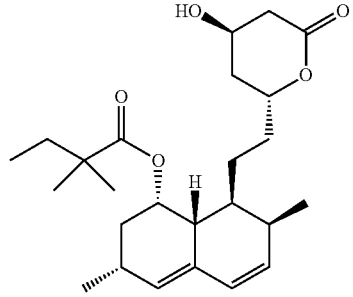

Formula II

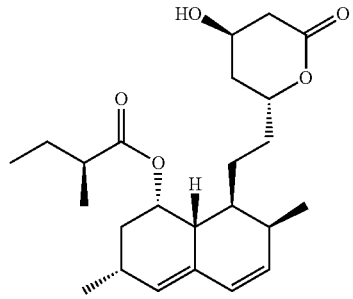

Formula III

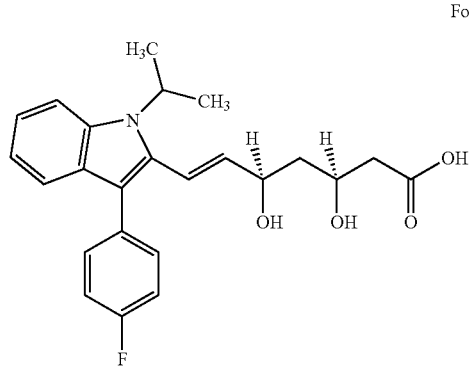

Formula IV

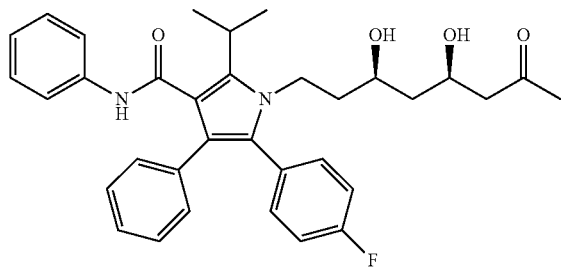

Formula V

In addition, the invention also provides the use in combination therapy with lipophilic statins any analogue or derivative of MTX that can be used as a therapeutic alternative to MTX and that acts with an action mechanism equal to or very similar to that of MTX. These include other pharmaceutical inhibitors of the dihydrofolate reductase enzyme such as trimetrexate (5-methyl-6-[(3,4,5-trimethoxyphenyl) aminomethyl] quinazoline-2,4-diamine, compound in Formula VI) and pemetrexed ((2S)-2-{[4-[2-(2-amino-4-oxo-1,7-dihydropyrrolo[2,3-d]pyrimidin-5-yl) ethyl]benzoyl]amino} pentanedioic acid, compound in Formula VII). As is evident to an expert in the field, these equivalents, analogues and derivatives of MTX are susceptible to interact with the lipophilic statins and see their effect strengthened by them, in the same way as MTX, and they, therefore, show the same advantages when used in therapy combined with them.

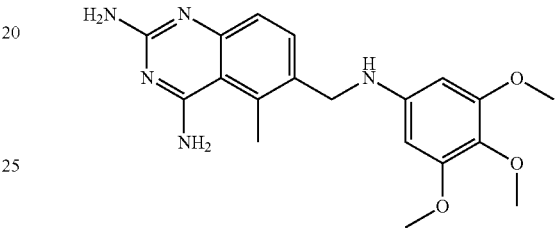

Formula VI

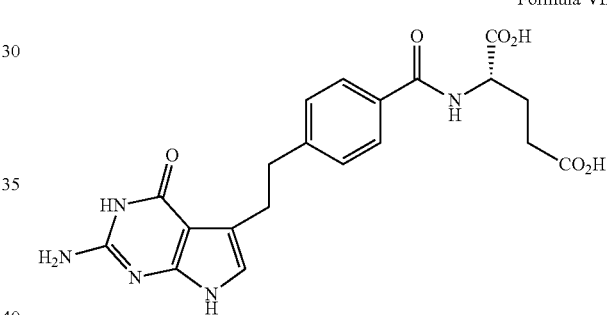

Formula VII

Any pharmaceutically acceptable salt of the DHFR inhibitor or an lipophilic statin inhibitor can be used for the purposes of the invention. The term "acceptable pharmaceutical salt" refers to salts prepared from non-toxic pharmaceutically acceptable bases. There is no limitation in relation to these salts, except that when used for therapeutic purposes they must be pharmaceutically acceptable.

The pharmaceutically acceptable salts of the compounds for the combination therapy of the invention can be prepared using well known methods in the state of the art. For example, they can be prepared from the parent compound, which contains an acidic or basic portion, using methods that are conventional in the practice of chemistry. These salts are generally prepared, for example, by reacting the free acid or base of these compounds with a stoichiometrically adequate amount of the acid or pharmaceutically acceptable salt in the presence of water, or an organic solvent or a mixture of both. When the salts are prepared from the basic parent compounds, these salts are prepared from the non-toxic pharmaceutically acceptable acids, including organic or inorganic acids. These acids include, for example, acetic acid, benzosulfonic, benzoic, camphorsulfonic, citric, ethanosulfonic, fumaric, gluconic, glutamic, hydrobromic, hydrochloric, lactic, maleic, malic, mandelic, methanosulfonic, phosphoric, succinic, sulfuric, tartaric, p-toluenosulfonic and similar.

The invention also incorporates those compounds for use in combination therapy that can be in their crystalline form, either compounds in free solvation or as solutions (for example, hydrates). The methods for solvation are known in the state of the art.

The present invention also provides the use of a prodrug of a DHFR inhibitor or of a lipophilic statin. "Prodrug" is understood as a substance that is administered in an inactive form (or less active) but that after administration is transformed into its corresponding pharmaceutically active ingredient as a consequence of the patient's normal metabolic processes. Specifically, the term prodrug refers to acceptable and physiologically hydrolysable esters.

The term "acceptable and physiologically hydrolysable ester" is understood an ester in which the hydroxyl group is esterified and which is hydrolysable under physiological conditions in order to give an acid that is physiologically tolerable at the administration dose. Examples of these esters include acetates and benzoates of MTX or of the lipophilic statins.

The invention also provides the administration of a DHFR inhibitor in a conjugated format with substances such as liposomes, glycerol, albumin, diglycerides, amino acids such as phenylalanine or proline or peptides such as arginine-glycine-asparagine or a "hairpin" peptide. The conjugation of the drug with these substances can increase their bioavailability.

In a specific embodiment, the DHFR inhibitor in the combination therapy of the invention is MTX. In another embodiment, the combination therapy of the invention is undertaken with MTX and simvastatin.

The combination therapy of the present invention provides an additional advantage that consists of the possibility of using the combination therapy not only for therapeutic purposes but also for preventative purposes, specifically, with the objective of preventing recurrences (or relapse) in the patients that have responded satisfactorily to previous treatment for cancer or autoimmune disease.

Additionally, another aspect of the invention provides a DHFR inhibitor selected from the group that consists of methotrexate, trimetrexate and pemetrexed; or a pharmaceutically acceptable salt thereof, for its use in the prevention of recurrences of a disease selected from the group consisting of cancer, psoriasis, psoriatic arthritis, juvenile polyarticular arthritis, rheumatoid arthritis, Crohn's disease, polymyositis, dermatomyositis and sarcoidosis, wherein said treatment comprises administering simultaneously, separately or sequentially to a subject a lipophilic statin and a DHFR inhibitor. This aspect can be reformulated as the use of an inhibitor of the dihydrofolate reductase enzyme selected from the group that consists of methotrexate, trimetrexate and pemetrexed; or a pharmaceutically acceptable salt thereof, for the preparation of a medicament for the prevention of the recurrences of a disease selected from the group consisting of cancer, psoriasis, psoriatic arthritis, juvenile polyarticular arthritis, rheumatoid arthritis, Crohn's disease, polymyositis, dermatomyositis and sarcoidosis, wherein said treatment or prevention comprises administering simultaneously, separately or sequentially to a subject a lipophilic statin and an inhibitor of the dihydrofolate reductase enzyme. The present invention also provides a method for the prevention of the recurrences of a disease selected from the group consisting of cancer, psoriasis, psoriatic arthritis, juvenile polyarticular arthritis, rheumatoid arthritis, Crohn's disease, polymyositis, dermatomyositis and sarcoidosis, in a patient that requires it, wherein said treatment method consists of the administration to a subject in a manner simultaneous, separate or sequential of a lipophilic statin and an inhibitor of the dihydrofolate reductase enzyme selected from the group that consists of methotrexate, trimetrexate and pemetrexed; or a pharmaceutically acceptable salt thereof.

The side effect of the use and administration of DHFR inhibitors such as MTX following current clinical practice are considerable, to the extent that their use is not contemplated in patients wherein the pathology is in remittance or has disappeared thanks to a previous treatment. Having the ability to use lower concentrations of, for example MTX with greater therapeutic efficacy, the combination therapy of the invention can be used to avoid a recurrences in the patient that has responded to a previous therapy for the treatment of a disease that benefits from the administration of MTX, such as, for example, a cancer. In this sense it is important to indicate that the inventor has found that the strengthening of the effect on the DHFR inhibitor by the lipophilic statin is particularly relevant at low doses, particularly at MTX doses comprising 1 to 3 $mg/m^2$ of the patient's body surface area.

The diseases susceptible to benefit from the present combination therapy of the invention include those diseases for which the administration of DHFR inhibitors, such as MTX, is indicated, particularly cancer and some autoimmune diseases. In a specific embodiment the combination therapy of the invention can be used for the treatment of a cancer selected from the group that consists of osteosarcoma, chorioademoma destruens, choriocarcinoma, hydatidiform mole, acute lymphocytic leukaemia, acute non-lymphocytic leukaemia, large cell lymphoma, high-grade lymphoma, non-Hodgkin's lymphoma, lymphosarcoma, Burkitt's lymphoma, cutaneous T cell lymphoma, pleural mesothelioma, breast cancer, ovarian cancer, squamous head tumour, squamous neck tumour, small cell lung carcinoma, urinary bladder cancer. In a specific embodiment, the combination therapy of the invention is for the treatment of osteosarcoma. In another specific embodiment the cancer is acute lymphocytic leukaemia.

Another group of diseases that can benefit from the combination therapy of the invention containing a DHFR inhibitor and lipophilic statins consists of some autoimmune diseases, particularly psoriasis, psoriatic arthritis, juvenile polyarticular arthritis, rheumatoid arthritis, Crohn's disease, polymyositis, dermatomyositis and sarcoidosis.

As will be evident for an expert in the field, the present combination therapy of the invention is effective not only when the active ingredients, the DHFR inhibitor and the lipophilic statins, are used in a single composition, but also when two different compositions are used, whether administered simultaneously or separately in any order and with a therapeutically effective range. In addition, an expert in the field will understand that the DHFR inhibitor can be prescribed by a medical specialist for use along with a lipophilic statin in a combination therapy with the purpose of treating or preventing the recurrences of a disease that benefits from the administration of the DHFR inhibitor and vice versa.

Therefore, one aspect of the invention refers to a DHFR enzyme inhibitor selected from the group consisting of methotrexate, trimetrexate and pemetrexed; or a pharmaceutically acceptable salt thereof, for its use in the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis when used in combination treatment with a lipophilic statin. This aspect can be reformulated as the use of an DHFR inhibitor selected from the group that consists of methotrexate, trimetrexate and pemetrexed; or a pharmaceutically acceptable salt thereof, for the preparation of a medicament for the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis, wherein said medicament is for use in combination therapy with a lipophilic statin. The invention also refers to a method for the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis in a patient that requires it, wherein said treatment method comprises administering to a subject a DHFR inhibitor selected from the group that consists of methotrexate, trimetrexate and pemetrexed; or a pharmaceutically acceptable salt thereof, in a combination therapy with a lipophilic statin.

Another aspect of the invention refers to a DHFR inhibitor selected from the group consisting of methotrexate, trimetrexate and pemetrexed; or a pharmaceutically acceptable salt thereof, for its use in the prevention of the recurrences of cancer when used in combination treatment with a lipophilic statin. This aspect can be reformulated as the use of MTX, a prodrug, or a pharmaceutically acceptable salt thereof, for the preparation of a medicament for the prevention of the recurrences of a disease selected from the group consisting of cancer, psoriasis, psoriatic arthritis, juvenile polyarticular arthritis, rheumatoid arthritis, Crohn's disease, polymyositis, dermatomyositis and sarcoidosis, wherein said medicament is for use in combination therapy with a lipophilic statin. The invention also refers to a method for the prevention of the recurrences of a disease selected from the group consisting of cancer, psoriasis, psoriatic arthritis, juvenile polyarticular arthritis, rheumatoid arthritis, Crohn's disease, polymyositis, dermatomyositis and sarcoidosis, in a patient that requires it, wherein said treatment method comprises administering to a subject a DHFR inhibitor selected from the group that consists of methotrexate, trimetrexate and pemetrexed; or a pharmaceutically acceptable salt thereof, in a combination therapy with a lipophilic statin.

In addition the present invention provides a DHFR inhibitor selected from the group consisting of methotrexate, trimetrexate and pemetrexed; or a pharmaceutically acceptable salt thereof and of a lipophilic statin for use in the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis. This aspect can be reformulated as the use of a DHFR inhibitor selected from the group consisting of methotrexate, trimetrexate and pemetrexed; or a pharmaceutically acceptable salt thereof and of a lipophilic statin for the preparation of a medicament for the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis. The invention also provides a method for the treatment of a disease selected from the group consisting of cancer, psoriasis, psoriatic arthritis, juvenile polyarticular arthritis, rheumatoid arthritis, Crohn's disease, polymyositis, dermatomyositis and sarcoidosis in a patient that requires it, wherein said method comprises administering to a subject a DHFR inhibitor selected from the group that consists of methotrexate, trimetrexate and pemetrexed; or a pharmaceutically acceptable salt thereof and a lipophilic statin.

In another aspect, the invention provides a DHFR inhibitor selected from the group consisting of methotrexate, trimetrexate and pemetrexed; or a pharmaceutically acceptable salt thereof and of a lipophilic statin, for use in the prevention of the recurrences of a disease selected from the group consisting of cancer, psoriasis, psoriatic arthritis, juvenile polyarticular arthritis, rheumatoid arthritis, Crohn's disease, polymyositis, dermatomyositis and sarcoidosis. This aspect can be reformulated as the use of a DHFR inhibitor selected from the group consisting of methotrexate, trimetrexate and pemetrexed; or a pharmaceutically acceptable salt thereof and of a lipophilic statin, for the preparation of a medicament for the prevention of the recurrences of a disease selected from the group consisting of cancer, psoriasis, psoriatic arthritis, juvenile polyarticular arthritis, rheumatoid arthritis, Crohn's disease, polymyositis, dermatomyositis and sarcoidosis. The invention also provides a method for the prevention or the recurrences of a disease selected from the group consisting of cancer, psoriasis, psoriatic arthritis, juvenile polyarticular arthritis, rheumatoid arthritis, Crohn's disease, polymyositis, dermatomyositis and sarcoidosis in a patient that requires it, wherein said method comprises administering to a subject a DHFR inhibitor selected from the group that consists of methotrexate, trimetrexate and pemetrexed; or a pharmaceutically acceptable salt thereof and a lipophilic statin.

The present invention envisages that in the combination therapy the DHFR inhibitor and the lipophilic statin are administered simultaneously. The invention also envisages that the DHFR inhibitor and the lipophilic statin are administered separately, in any order and with a therapeutically effective range. The therapeutically effective range will, to a great extent, depend on the disease considered and whether the purpose is treatment or the prevention or recurrences, but always taking into consideration the fact that thanks to the combination with the lipophilic statin the amount of DHFR inhibitor administered to the patient is much less that in the conventional treatment.

When the DHFR inhibitor used in the combination therapy of the invention is MTX, the dose administered of this drug can be comprised from 0.5 mg/m$^2$ of the patient's surface area to 20 g/m$^2$ of the patient's surface area and the dose of lipophilic statin can be comprised from 10 to 100 mg. The approximate dose will depend on the patient's disease and whether the purpose of the therapy is treatment or the prevention or recurrences. Therefore, for the treatment of acute lymphocytic leukaemia the dose of MTX administered can comprise from 1 to 3 mg/m$^2$ of the patient's surface area. For the treatment of osteosarcoma a dose of MTX can be administered comprising from 12 to 15 mg/m$^2$ of the patient's surface area. In both cases, it is possible to administer an initial high dose of lipophilic statin comprising from 40 to 80 mg and a maintenance dose comprising from 10 to 30 mg, for example, 20 mg. For the prevention of recurrences of osteosarcoma it is possible to administer a dose that contains 3-20 mg/m$^2$ of the patient's surface area of MTX and 20 mg of lipophilic statin. Similarly, the administration regime will depend on the disease in question and whether the objective is the treatment or the prevention of recurrences of this disease. In general, in the combination therapy of the present invention the MTX can be administered with a frequency comprising 1 to 5 weeks and the lipophilic statin can be administered with a frequency comprising 1 to 7 days. For example, when the objective of the combination therapy is the treatment of acute lymphocytic leukaemia, it is possible to administer an MTX dose comprising from 1 to 3 mg/m$^2$ of the patient's surface area for 4-6 weeks. For example, when the objective of the combination therapy is the treatment of osteosarcoma, it is possible to administer an MTX dose comprising from 12 to 15 mg/m² of the patient's surface area every 14 days. In both cases, it is possible to administer an initial high dose of lipophilic statin comprising from 40 to 80 mg and a maintenance dose comprising from 10 to 30 mg. For example, 20 mg. For example, when the objective of the therapy of the invention is for the prevention of the recurrences of osteosarcoma, it is possible to administer a dose that contains 3-20 mg/m² of the patient's surface area of MTX and 20 (mg) of lipophilic statin each week.

As previously mentioned, the MTX and the lipophilic statin in the sense of the combination therapy of the invention can be administered simultaneously, sequentially or separately. In the case where the administration may be simultaneous, the drugs can form part of the same pharmaceutical composition or each drug can form part of a different pharmaceutical composition.

An aspect of the invention provides a pharmaceutical composition that comprises an inhibitor of the dihydrofolate reductase enzyme selected from the group consisting of methotrexate, trimetrexate and pemetrexed; or a pharmaceutically acceptable salt thereof; and of a lipophilic statin along with excipients and/or pharmaceutically acceptable vehicles. This composition is effective for use in the combination therapy of the invention for the treatment or prevention of recurrences of the diseases mentioned above.

The expression "excipients and/or pharmaceutically acceptable vehicles" refers to materials, compositions or pharmaceutically acceptable vehicles. Each component must be pharmaceutically acceptable in the sense of being compatible with the other ingredients in the pharmaceutical composition. They must also be suitable for use in contact with the tissues and organs of human beings and animals without producing excessive toxicity, irritation, allergic reactions, immunogenicity or other problems or complications consistent with a reasonable benefit/risk ratio.

In a specific embodiment, the lipophilic statin in the compositions of the invention is selected from the group consisting of methotrexate, trimetrexate and pemetrexed, or a pharmaceutically acceptable salt thereof. In another specific embodiment, the DHFR inhibitor is MTX. In a specific embodiment, the composition comprises MTX and simvastatin.

The composition of the invention can be formulated in a dosage unit for oral administration. In a specific embodiment, the dosage unit for oral administration is a tablet, pill, pastel, lozenge, capsule, solution, suspension, gel or jelly. In another embodiment, the composition of the invention is formulated in a dosage unit for administration intravenously, intramuscularly, transdermically, rectally, by an intracavitary route or by inhalation.

In a specific embodiment, the administration regime of the composition of the invention for the treatment of the aforementioned diseases will depend on the content of DHFR inhibitor and lipophilic statin in the dosage unit, as well as its indication. In establishing the administration regime of the composition of the invention the aforementioned dosage recommendations for the combination treatment must be taken into account.

When the administration of the DHFR inhibitor and lipophilic statin used in the combination therapy of the invention is sequential or separate, each drug will be formulated in a different composition and they will be administered in a kit along with suitable instructions for their administration in the treatment or in the prevention of recurrences of the aforementioned diseases.

Similarly, another instance of the invention provides a kit consisting of a first pharmaceutical composition consisting of a dihydrofolate reductase enzyme inhibitor selected from the group that consists of methotrexate, trimetrexate and pemetrexed; or a pharmaceutically acceptable salt thereof; a second pharmaceutical composition consisting of a lipophilic statin; and instructions for the use of both pharmaceutical compositions in a combination therapy for the treatment or the prevention of recurrences of group consisting of cancer, psoriasis, psoriatic arthritis, juvenile polyarticular arthritis, rheumatoid arthritis, Crohn's disease, polymyositis, dermatomyositis and sarcoidosis.

In an embodiment, the lipophilic statin in the kit in the invention is selected from the group that consists of atorvastatin, fluvastatin, lovastatin and pharmaceutically acceptable salts thereof. In a specific embodiment, the statin is simvastatin. In another embodiment the DHFR inhibitor is MTX.

Each active ingredient in the kit of the invention, the DHFR inhibitor and lipophilic statin, can be formulated in a dosage unit for oral administration. In a specific embodiment, the dosage unit for oral administration is a tablet, pill, pastel, lozenge, capsule, solution, suspension, gel or jelly. In another embodiment each active ingredient in the kit of the invention is formulated in a dosage unit for administration intravenously, intramuscularly, transdermically, rectally, by an intracavitary route or by inhalation.

A specific embodiment provides a kit consisting of MTX in a composition formulated in a dosage unit that contains 0.5 mg to 20 g of MTX along with excipients and pharmaceutically acceptable vehicles, a lipophilic statin in a composition formulated in a dosage unit that contains from 10 to 100 mg of lipophilic statin along with excipients and pharmaceutically acceptable vehicles and the instructions necessary for the administration of both pharmaceutical compositions in a combination therapy for the treatment or the prevention of recurrences of one of the aforementioned diseases. In an embodiment, the dosage unit of MTX contains from 1 to 3 mg of MTX. In another embodiment the dosage unit of MTX contains from 12 to 15 mg of MTX. In both cases the dosage unit of lipophilic statin can contain a high initial dose comprising from 40 to 80 mg or a maintenance dose comprising from 10 to 30 mg, for example 20 mg. These instructions for the administration of the compositions in combination therapy can indicate, among other things, that the compositions of MTX and lipophilic statin are administered simultaneously, or even, that they are administered separately following a therapeutically effective range. The instructions can also indicate the administration regime for the combination therapy, specifying the dosage units to be administered and the time intervals when each one should be administered. The dose and time intervals will depend on whether the kit is for the treatment of the disease or for the prevention of the relapse of the patient. In order to establish the administration regime of the composition of the invention the dose recommendations described above for the combined treatment of the invention must be taken into account.

The instructions can also indicate the disease to be treated using the combination therapy. In an embodiment the kit is for the treatment of cancer. In another embodiment the kit is for the prevention of recurrences in patients that have been treated for cancer. In a specific embodiment, the cancer is selected from a group that consists of osteosarcoma, chorioademoma destruens, choriocarcinoma, hydatidiform mole, acute lymphocytic leukaemia, acute non-lymphocytic leukaemia, large cell lymphoma, high-grade lymphoma, non-Hodgkin's lymphoma, lymphosarcoma, Burkitt's lymphoma, cutaneous T cell lymphoma, pleural mesothelioma, breast cancer, ovarian cancer, squamous head tumour, squamous neck tumour, small cell lung carcinoma, urinary bladder cancer. In a specific embodiment the cancer is osteosarcoma. In an embodiment the kit is for the treatment of an autoimmune disease. In a specific embodiment, the autoimmune disease is psoriasis, psoriatic arthritis, juvenile polyarticular arthritis, rheumatoid arthritis, Crohn's disease, polymyositis, dermatomyositis and sarcoidosis.

Throughout the description and the claim the word "comprise" and its variants does not preclude other technical characteristics, additives, components or steps. In addition the word "comprise" includes "consists of". For experts in the art, other objects, advantages and characteristics of the invention derive in part from the description and in part from the operation of the invention. The following examples and figures are provided by way of illustration and are not intended to be limiting of the present invention. In addition, the present invention includes all the possible combinations of specific and preferred embodiments described herein.

BRIEF DESCRIPTION OF THE FIGURES

FIG. 2: Representation of the table summarising the percentage survival for the treatment without (Column A) and with simvastatin (Column B) and the difference between both (Column C) for HOS cells treated with a simvastatin concentration of 0.5 µM. The column to the left represents the MTX dose used.

Figure 1:
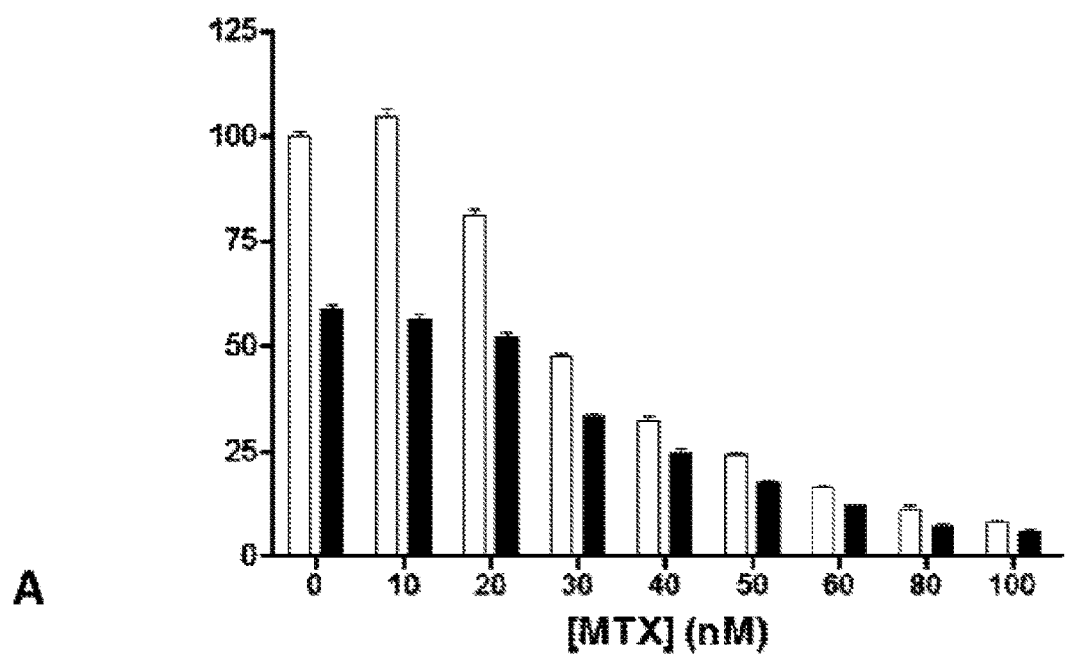
FIG. 1: Graphical representation of the cytotoxic effect on HOS cells of the combination treatment containing MTX and simvastatin. It was evaluated through the testing for sulforhodamine B, using a suboptimal fixed dose of simvastatin of 0.5 µM, combined with the MTX (black bars, Graph A; and black circles, Graph B) or using only increasing doses of MTX, to a maximum concentration of 100 nM for 48 hours (white bars, Graph A; and white circles Graph B) without the simvastatin. The measurements were made in triplicate and the data is represented using the mean±the standard deviation. The Y-axis represents survival expressed as a percentage and the X-axis the MTX concentration.
Figure 1:
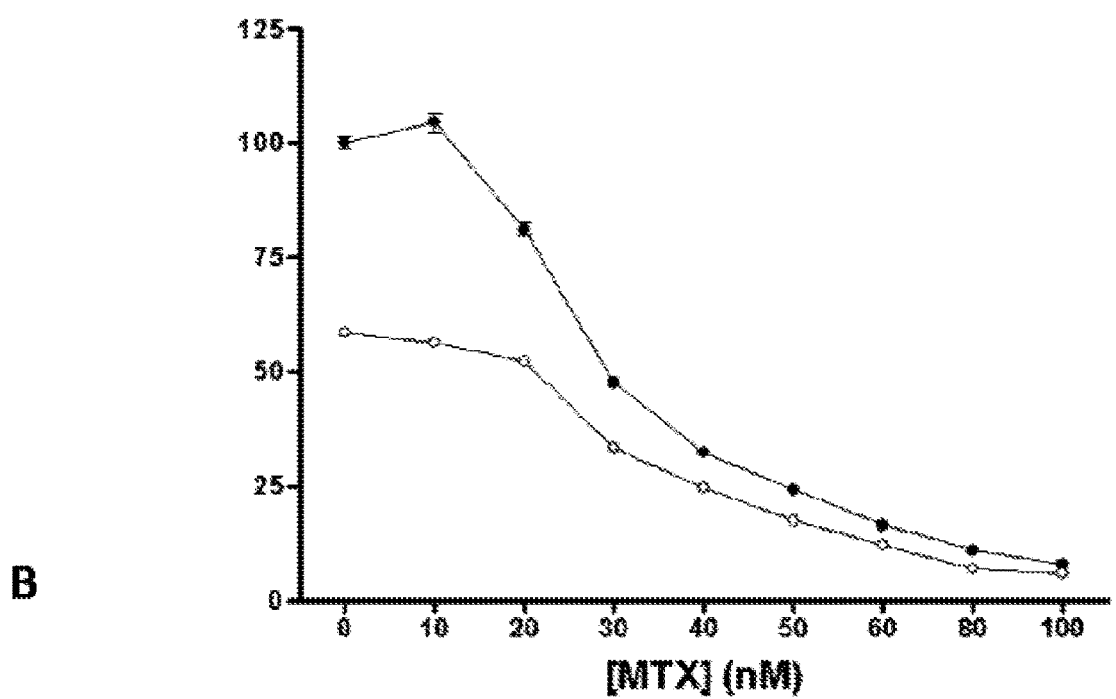
Figure 3:
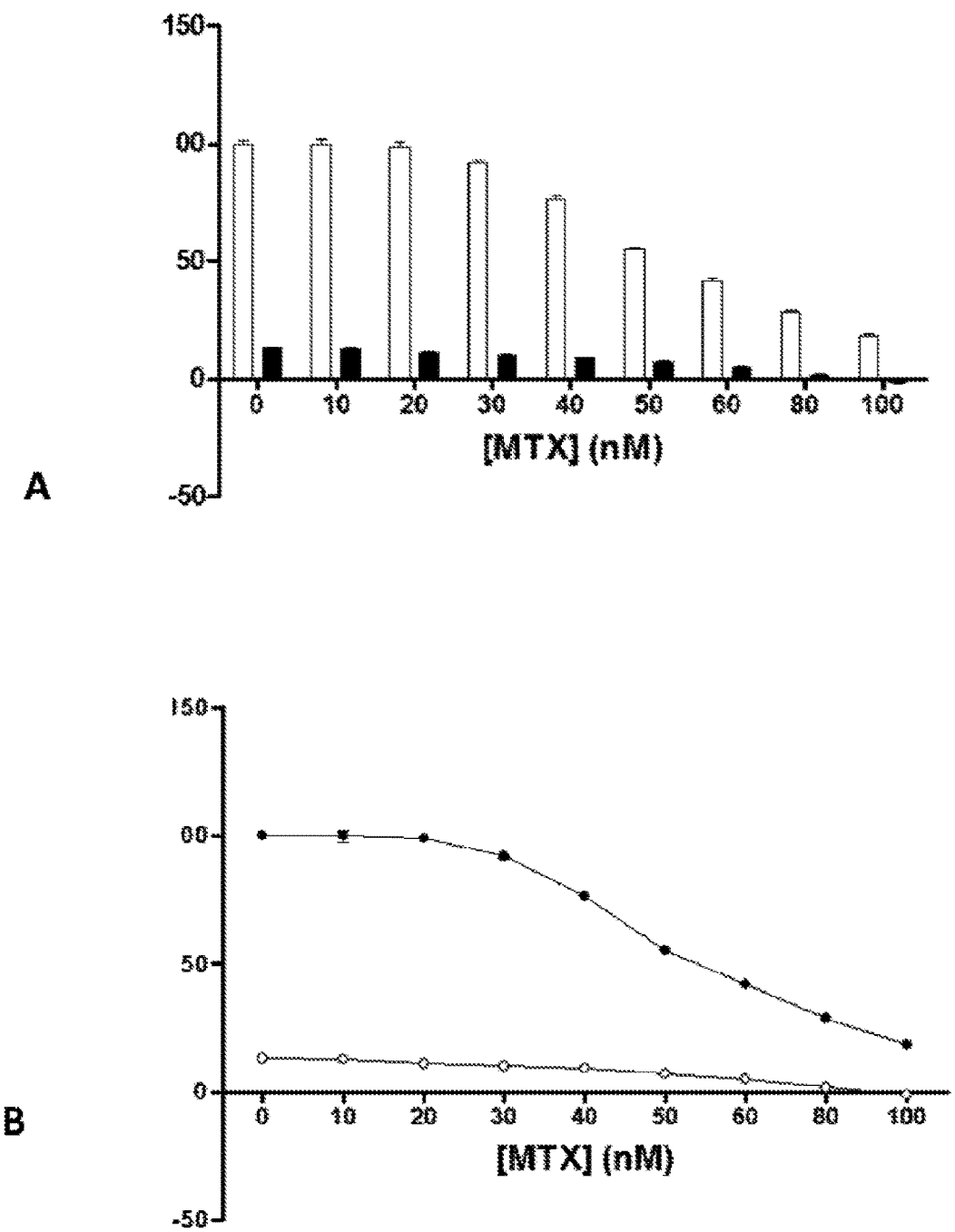
FIG. 3: Graphical representation of the cytotoxic effect on HOS cells of the combination treatment containing MTX and simvastatin. It was evaluated through the testing for sulforhodamine B, using a suboptimal fixed dose of simvastatin of 1 µM, combined with the MTX (black bars, Graph A; and black circles, Graph B) or using only increasing doses of MTX, to a maximum concentration of 100 nM for 48 hours (white bars, Graph A; and white circles Graph B) without the simvastatin. The measurements were made in triplicate and the data is represented using the mean±the standard deviation. The Y-axis represents survival expressed as a percentage and the X-axis the MTX concentration.
Figure 4:
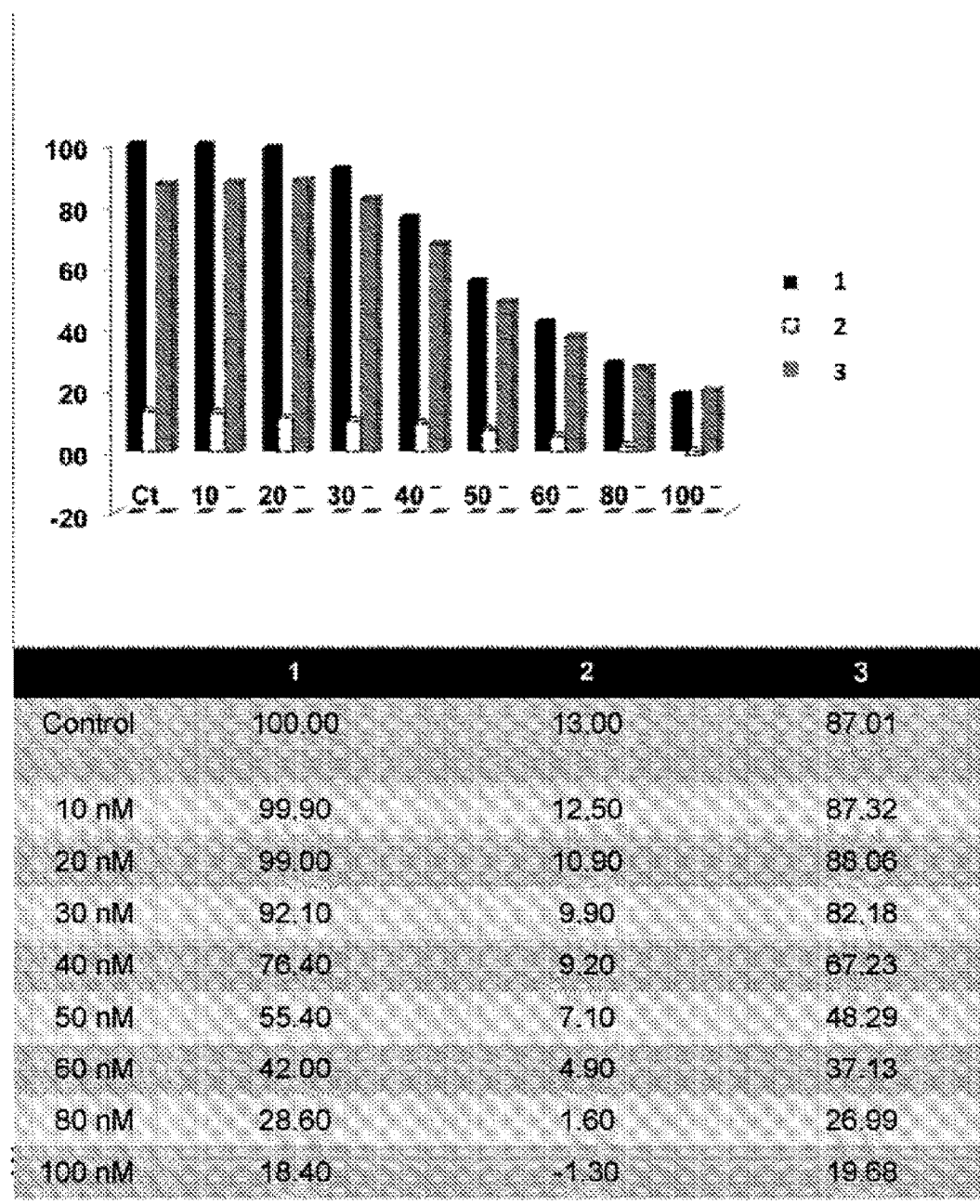
FIG. 4: Graphical representation (A) and table (B) summarising the percentage survival of HOS cells between the treatment without simvastatin (1) and with simvastatin (2) and the difference between both (3) to a concentration of 1 µM simvastatin. The column on the left represents the MTX dose used.
Figure 5:
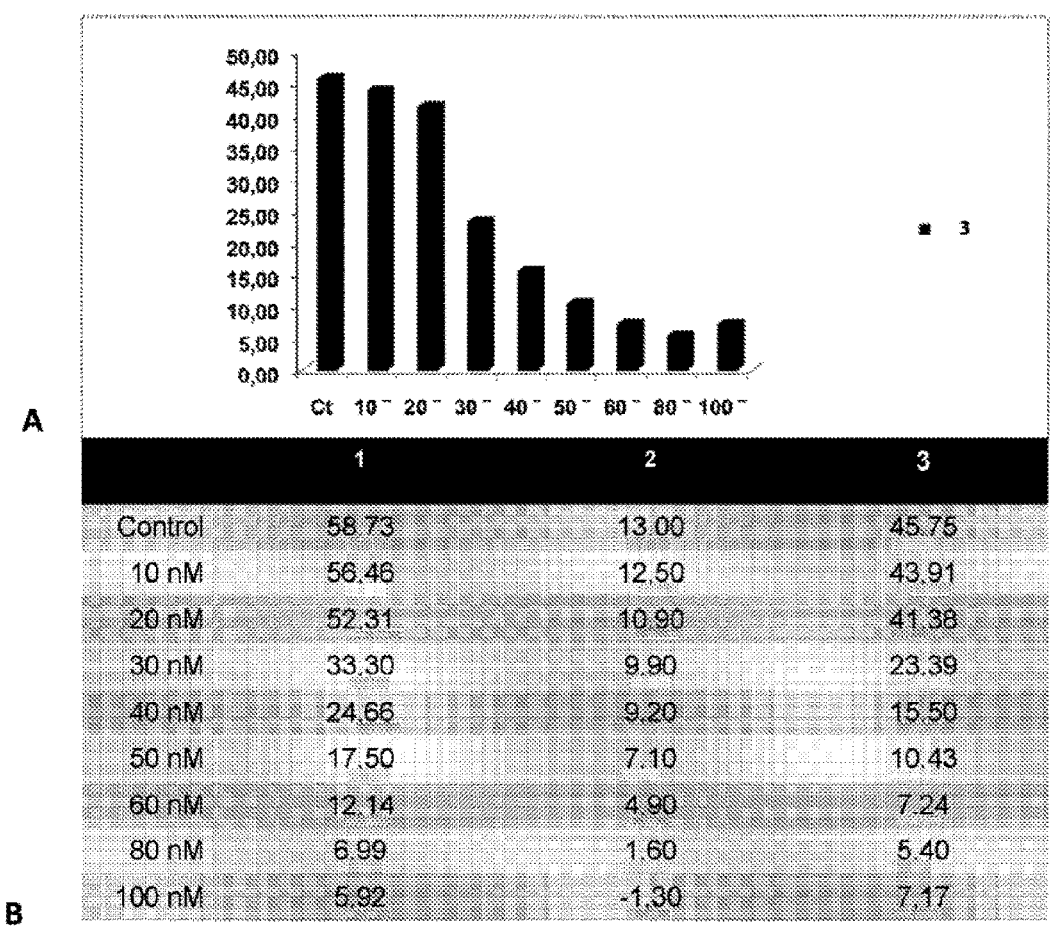
FIG. 5: Graphical representation (A) table (B) summarising the difference between (3) the percentage survival of HOS cells between the treatments with simvastatin at concentration of 0.5 µM (1) and a concentration of 1 µM (2). The column on the left represents the MTX dose used.
Figure 6:
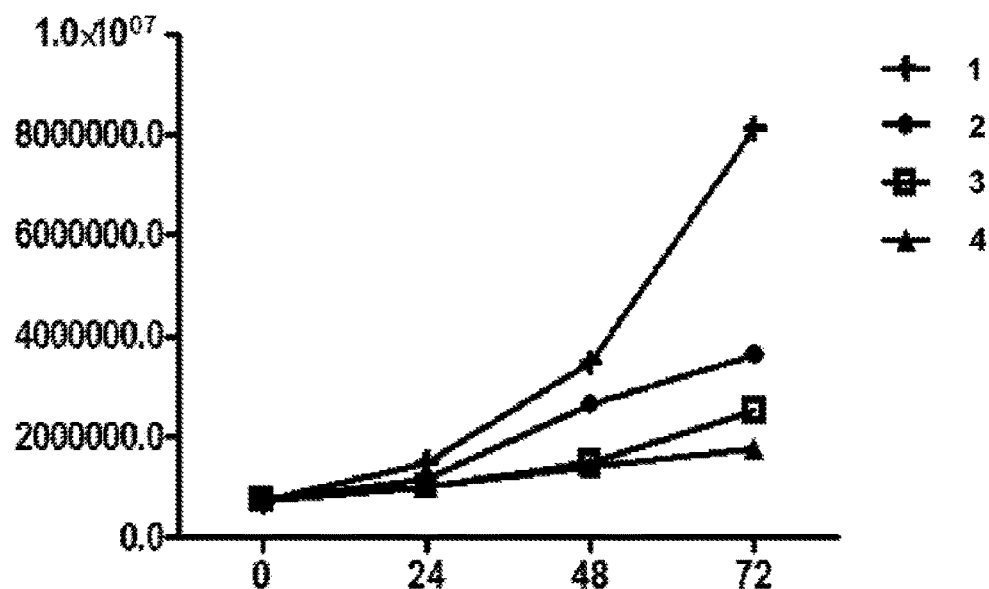
FIG. 6: Graphical representation evaluating the proliferative capacity of osteosarcoma cells (HOS) submitted to treatment with 0.5 µM simvastatin (2), with 50 nM methotrexate (3) or with both (4) in relation to control cells (1) over 72 hours (X-axis). The effect was evaluated by counting the total number of cells (viable and non-viable) in the Neubauer chamber (Y-axis) using the technique of staining with Tripan Blue. The measurements were made in triplicate and the data is represented using the mean±the standard deviation.
Figure 7:
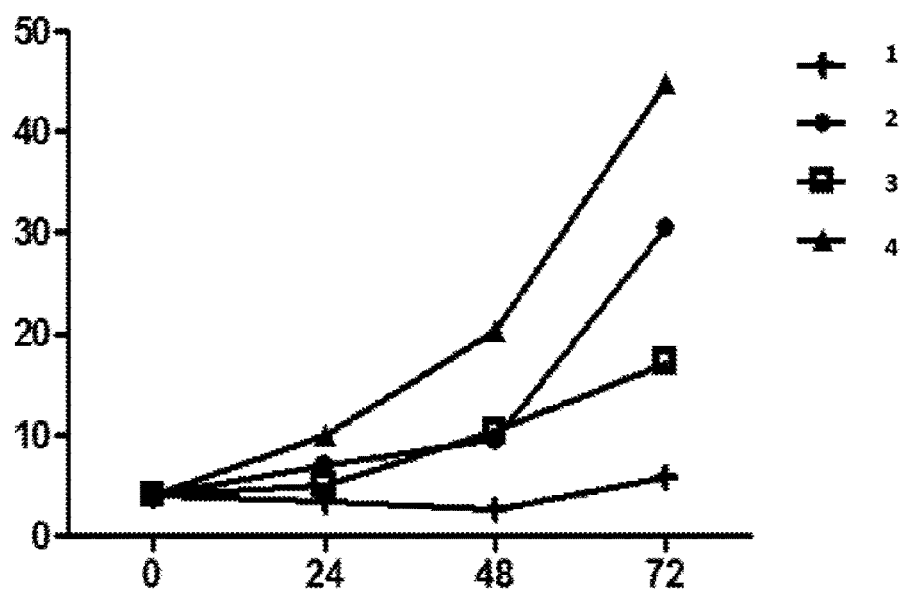
FIG. 7: Graphical representation evaluating the induction of cell death of osteosarcoma cells (HOS) submitted to treatment with 0.5 µM simvastatin (2), with 50 nM methotrexate (3) or with both (4) in relation to control cells (1) over 72 hours (X-axis). The effect was evaluated by counting the total number of non-viable cells in the Neubauer chamber (Y-axis) using the technique of staining with Tripan Blue. The measurements were made in triplicate and the data is represented using the mean±the standard deviation.
Figure 8A:
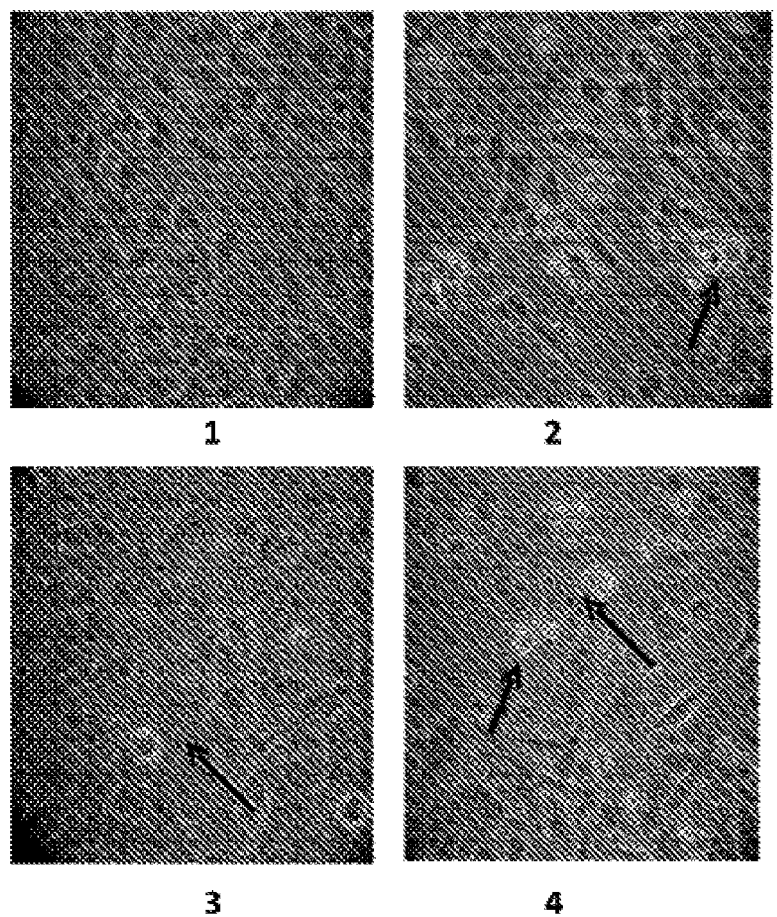
FIG. 8: Graphical representation of the morphological changes in the osteosarcoma cells (HOS) submitted to treatment with 0.5 µM simvastatin (2), with 50 nM methotrexate (3) or with both (4) in relation to control cells (1) over 48 hours (Panel A) and 72 hours (Panel B). It can be seen that the MTX (3) produces enlarged cells and even those with two nuclei (solid arrow); the SV (2) produces rounded cells (broken arrow); and both drugs (4) produced both effects.
Figure 8B:
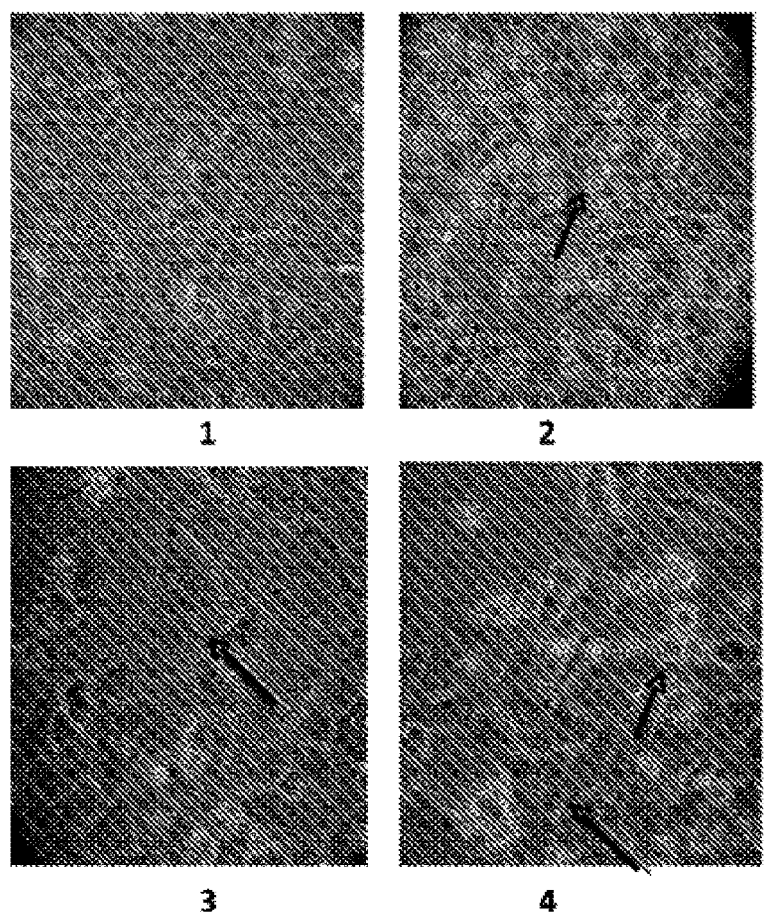
Figure 9:
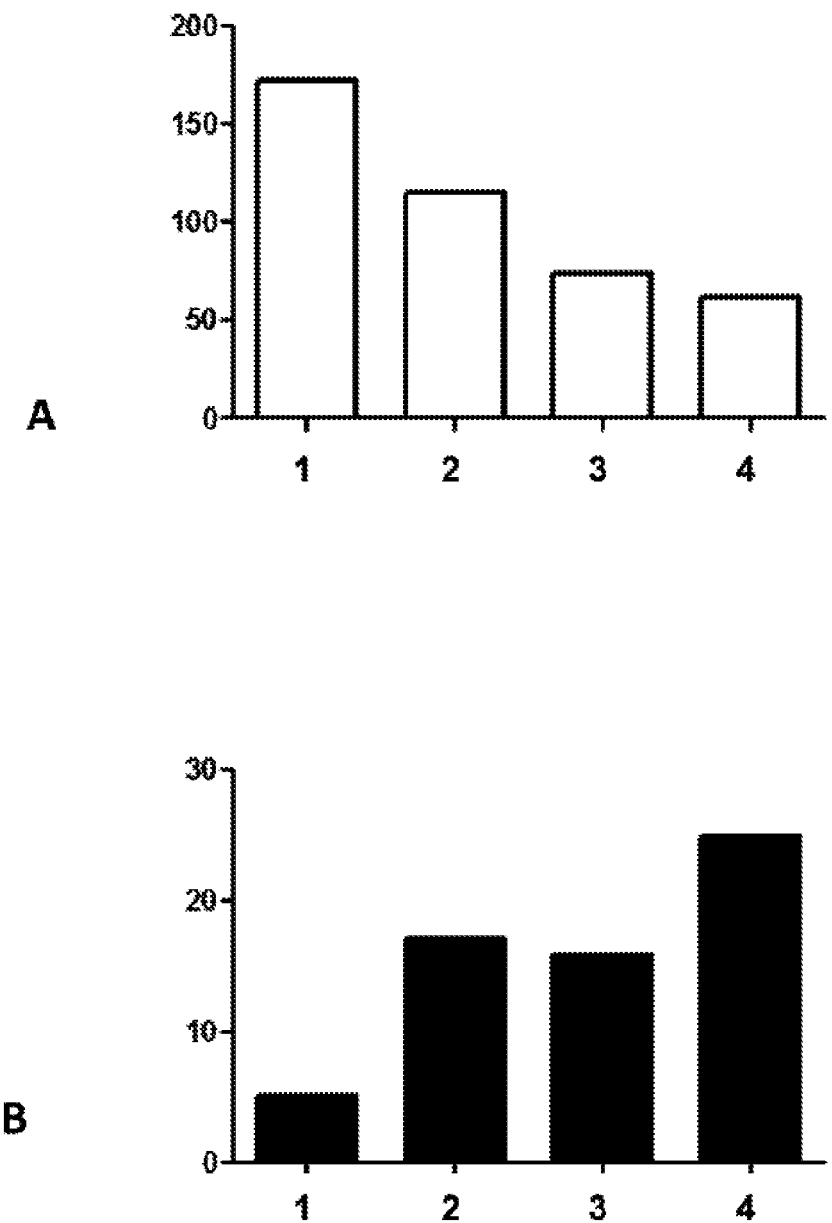
FIG. 9: Graphical representation of the change in the total number of osteosarcoma cells (HOS) (A) or the number of dead cells (B) submitted to treatment with 1 µM simvastatin (2), with 100 nM methotrexate (3) or with both (4) in relation to control cells (1) over 48 hours (X-axis). The effect was evaluated by counting the total number of cells (Y-axis in Graph A) and the Tripan Blue positive cells (Y-axis in Graph B) in the Neubauer chamber using the technique of staining with Tripan Blue. The measurements were made in triplicate and the data is represented using the mean±the standard deviation.
Figure 10:
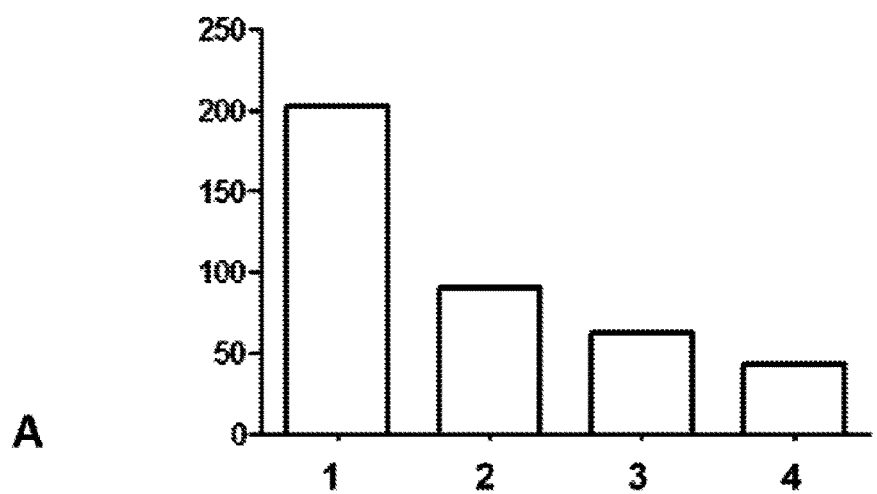
FIG. 10: Graphical representation of the change in the total number of osteosarcoma cells (HOS) (A) or the number of dead cells (B) submitted to treatment with 0.5 µM simvastatin (2), with 50 nM methotrexate (3) or with both (4) in relation to control cells (1) over 72 hours (X-axis). The effect was evaluated by counting the total number of cells (Y-axis in Graph A) and the Tripan Blue positive cells (Y-axis in Graph B) in the Neubauer chamber using the technique of staining with Tripan Blue. The measurements were made in triplicate and the data is represented using the mean±the standard deviation.
Figure 10:
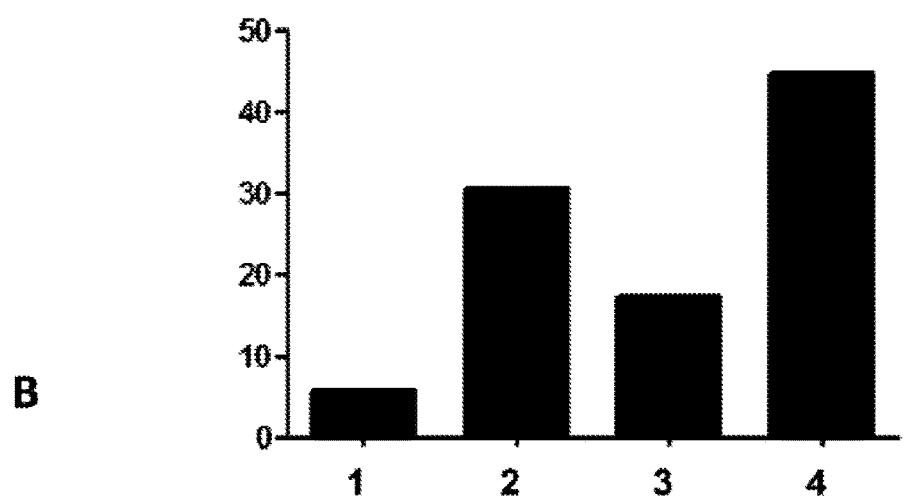
Figure 11:
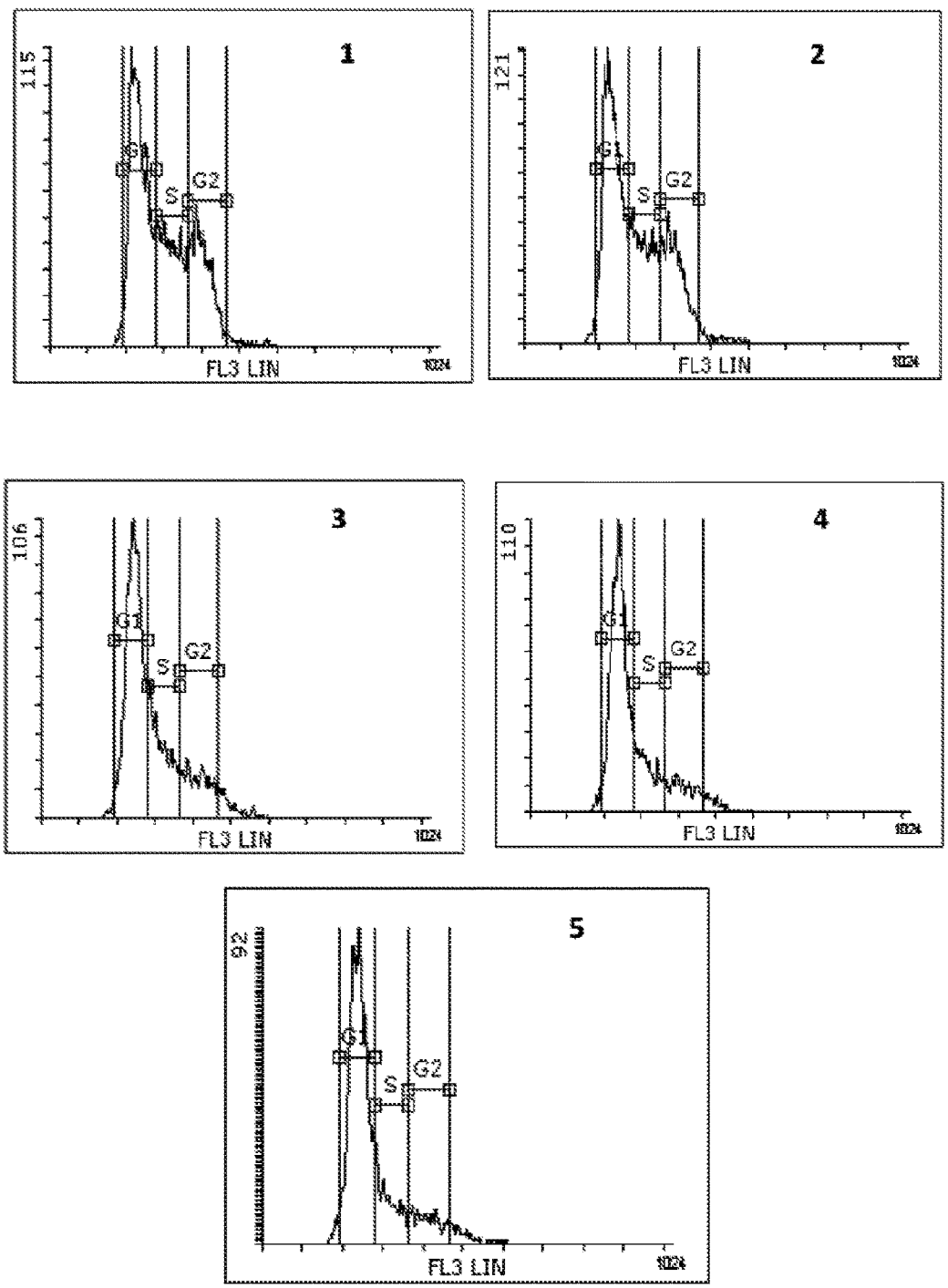
FIG. 11: Graphical representation of the changes in the cell cycle of the HOS cells treated with increasing doses of MTX for 24 hours. G1.1=control (in all the figures control implies 0 nM); 2=10 nM; 3=50 nM; 4=100 nM; 5=200 nM. Note the decrease in the S phase and in the number of cells in phase G2/M, with subsequent accumulation in the phase G1.
Figure 12:
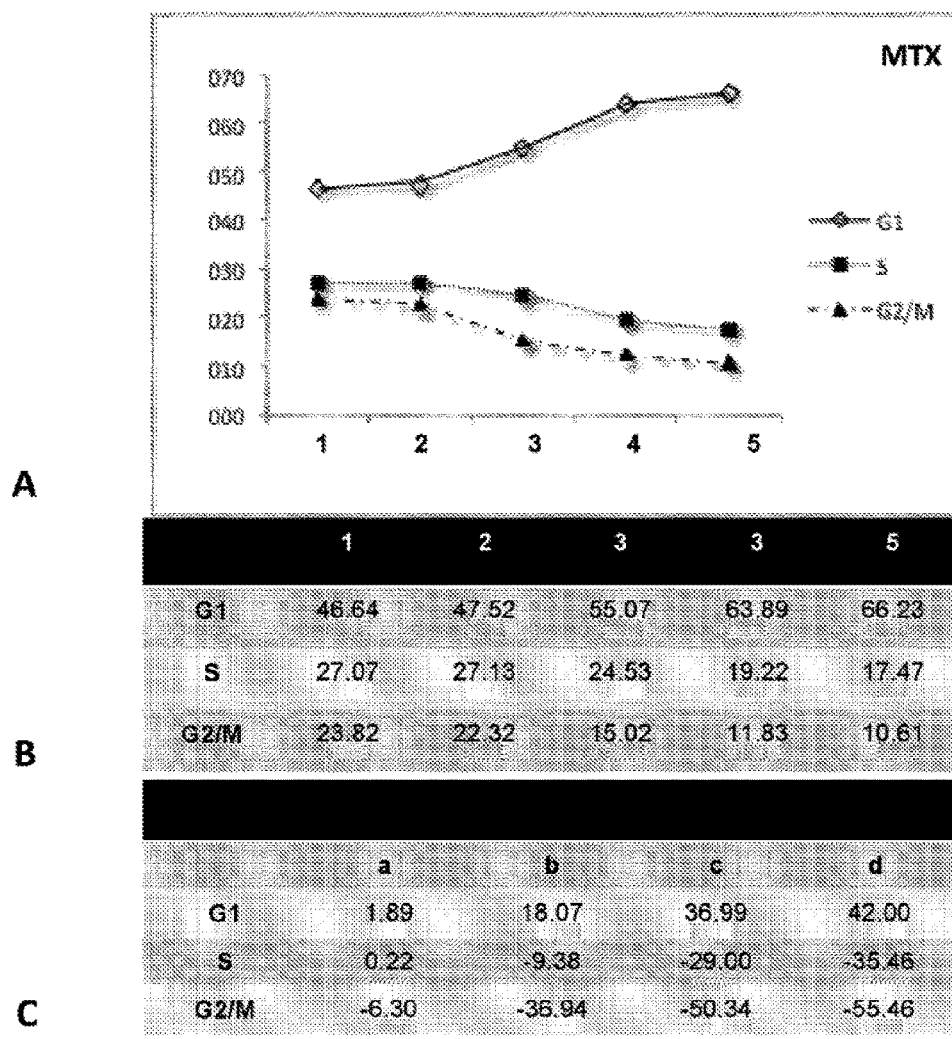
FIG. 12: (A) Graphical representation of the changes in the cell cycle of the HOS cells treated with increasing doses of MTX for 24 hours. The X-axis shows the concentrations of MTX: 1=control; 2=10 nM; 3=50 nM; 4=100 nM; 5=200 nM. (B) Absolute values in each of the cycle phases at the aforementioned MTX concentrations. (C) Percentage differences for the values obtained in each phase of the cycle compared to the control. a=10 nM vs. control; b=50 nM vs. control; c=100 nM vs. control; d=200 nM vs. control. The decrease in the S phase varies between 9.38% and 35.46% compared to the control. The G2/M phase decreases by between 6.30% and 55.46% compared to the control, while the cells in the G1 phase increase their number by between 1.89% and 42.00% compared to the control.
Figure 13:
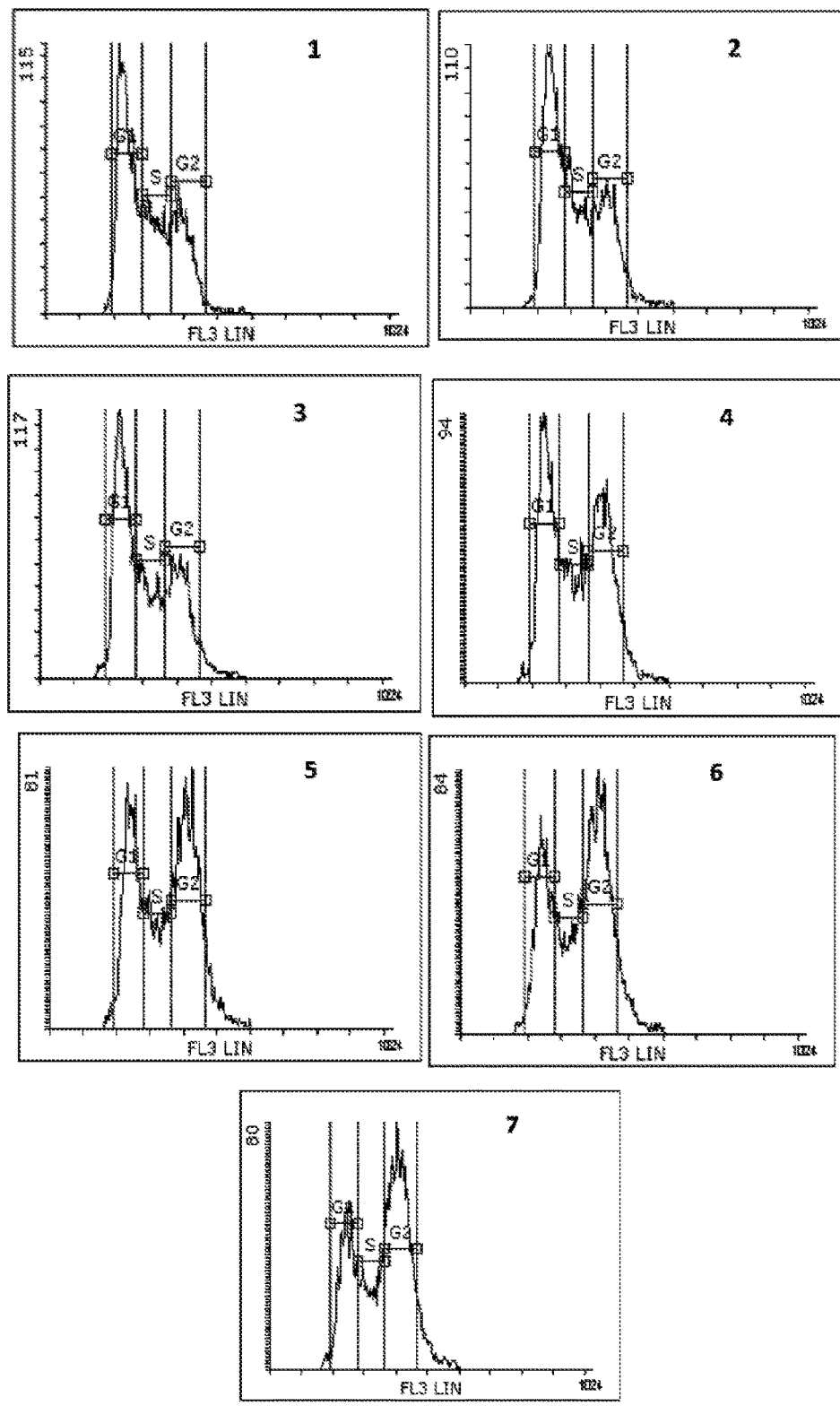

FIG. 13: Graphical representation of the changes in the cell cycle of the HOS cells treated with increasing doses of SV for 24 hours. 1=control; 2=0.2 µM; 3=0.5 µM; 4=1 µM; 5=2 µM; 6=5 µM; and 7=10 µM. The decrease in the S phase and in the number of cells in phase G1 is notable, with subsequent accumulation in the phase G2/M.

Figure 14:
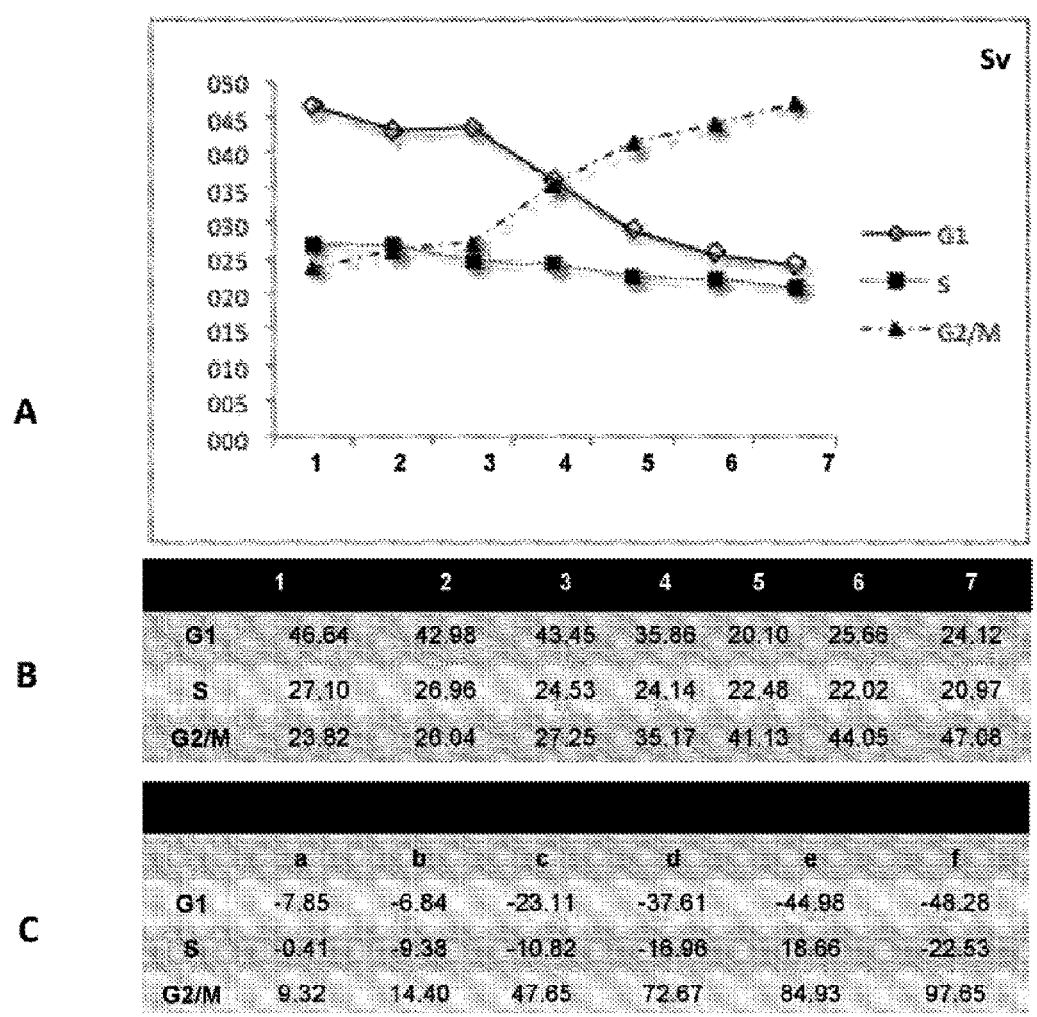

FIG. 14: (A) Graphical representation of the changes in the cell cycle of the HOS cells treated with increasing doses of SV for 24 hours. The X-axis shows the concentrations of SV: 1=control; 2=0.2 µM; 3=0.5 µM; 4=1 µM; 5=2 µM; 6=5 µM; and 7=10 µM. (B) Absolute values in each of the cycle phases at the aforementioned SV concentrations. (C) Percentage differences for the values obtained in each phase of the cycle compared to the control. a=0.2 µM vs. control; b=0.5 µM vs. control; c=1 µM vs. control; d=2 µM vs. control; e=5 µM vs. control; and f=10 µM vs. control. The decrease in the S phase varies between 0.41% and 22.53% compared to the control. The decreases in the G1 phase by between 7.85% and 48.28% compared to the control. The cells in the G2/M phase increase their number by between 9.32% and 97.65% compared to the control.

Figure 15:
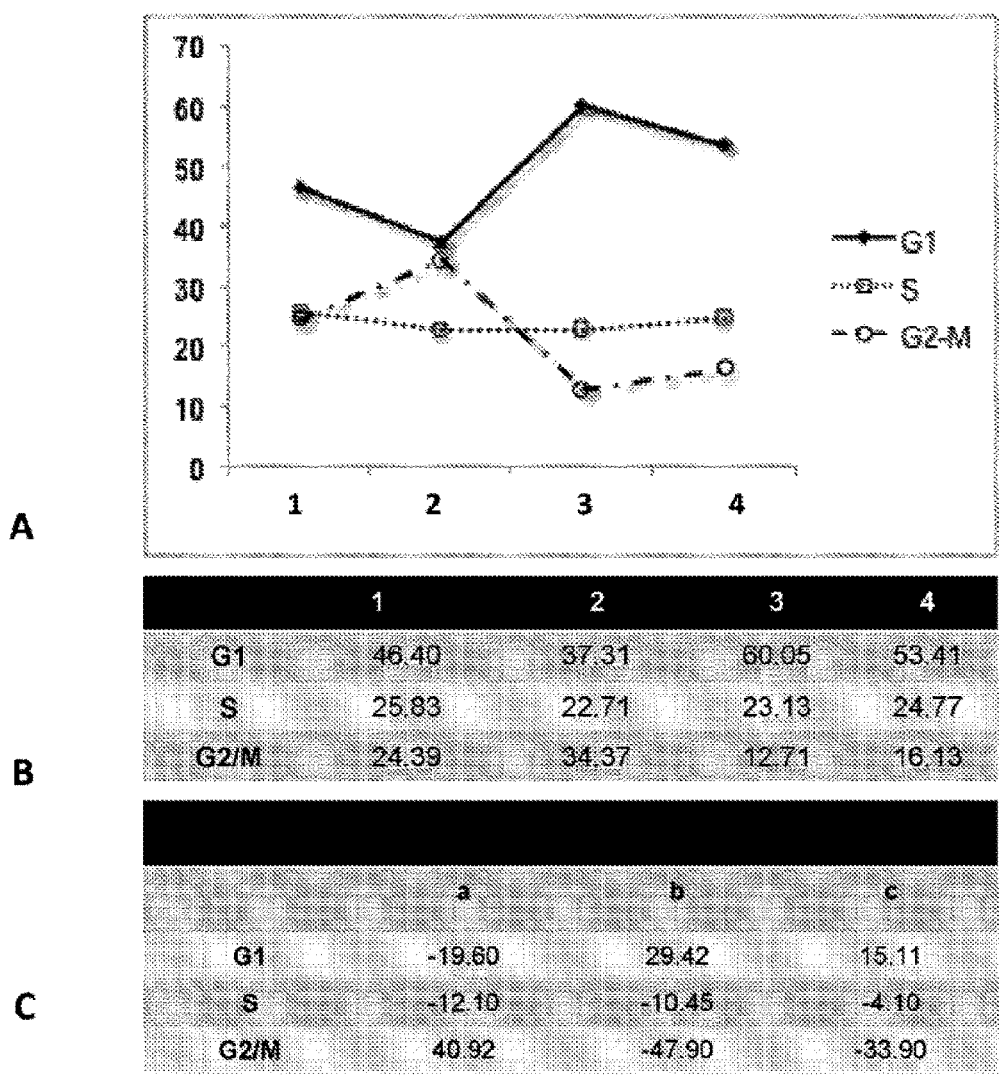

FIG. 15: (A) Graphical representation of the changes in the cell cycle of the HOS cells treated with a combination of SV and MTX for 24 hours. The X-axis shows the concentrations of the drugs: 1=control; 2=SV 1 µM; 3=MTX 50 nM; 4=SV 1 µM+MTX 50 nM; (B) Absolute values in each of the cycle phases at the aforementioned concentrations. (C) Percentage differences for the values obtained in each phase of the cycle compared to the control. a=SV 1 µM vs. control; b=MTX 50 nM vs. control; c=both vs. control. The decrease in the S phase varies between 4.10% and 12.10% compared to the control. The G1 phase decreases by 19.60% with SV, but increases 15.11% compared to the control when combined with MTX. The cells in the G2/M phase increase their number by 40.92% when treated with SV alone, but decrease by 33.90% compared to the control when combined with MTX.

Figure 16:
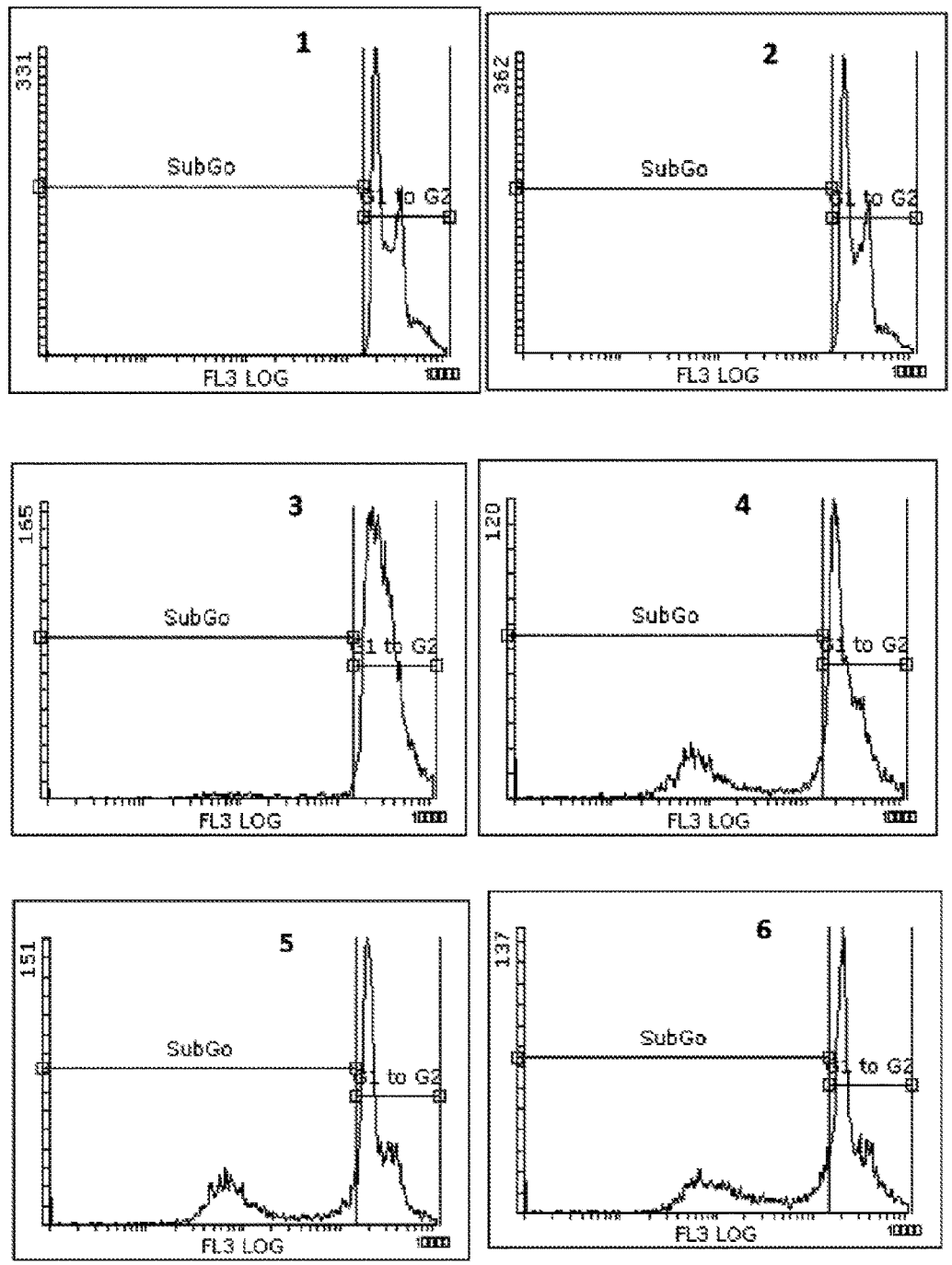

FIG. 16: Graphical representation of the SubG0 peak for the HOS cells treated with MTX for 48 hours. 1=control; 2=MTX 10 nM; 3=MTX 20 nM; 4=MTX 50 nM; 5=MTX 100 nM; 6=MTX 200 nM. There is a noticeably significant change in the profile of the G1-G2/M region and the incipient appearance of the SubG0 peak at an MTX concentration of 20 NM (3), indicative of cell death by apoptosis.

Figure 17:
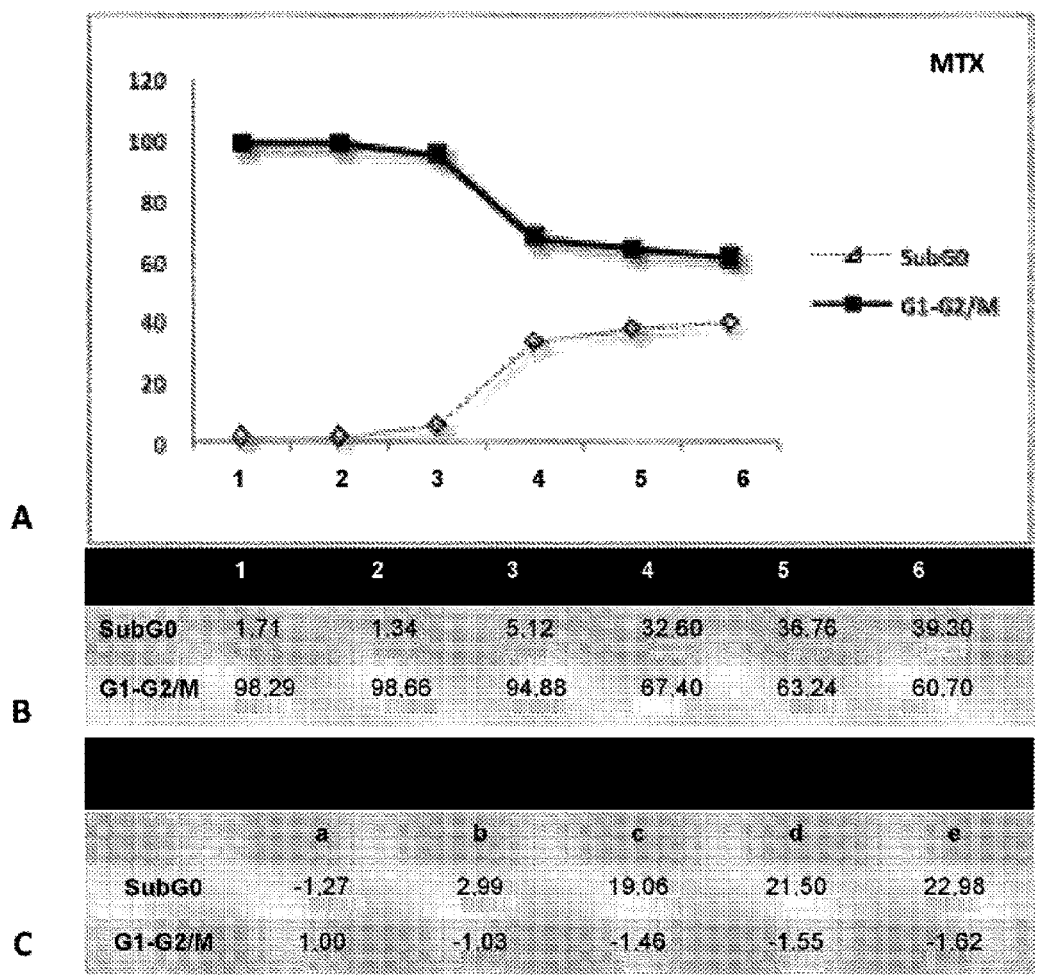

FIG. 17: (A) Graphical representation of the changes in the SubG0 peak in the G1-G2/M region of the HOS cells treated with increasing doses of MTX for 48 hours. The X-axis shows the concentrations of MTX: 1=control; 2=10 nM; 3=20 nM; 4=50 nM; 5=100 nM; 6=200 nM. (B) Absolute values in each of the regions studies at the aforementioned MTX concentrations. (C) Increases or decreases in the values obtained for each of the regions studied compared to the control. a=10 nM vs. control; b=20 nM vs. control; c=50 nM vs. control; d=100 nM vs. control; and e=200 nM vs. control. The most notable result is the significant increase in the number of cells quantified in the SubG0 phase at does above 50 nM of MTX.

Figure 18:
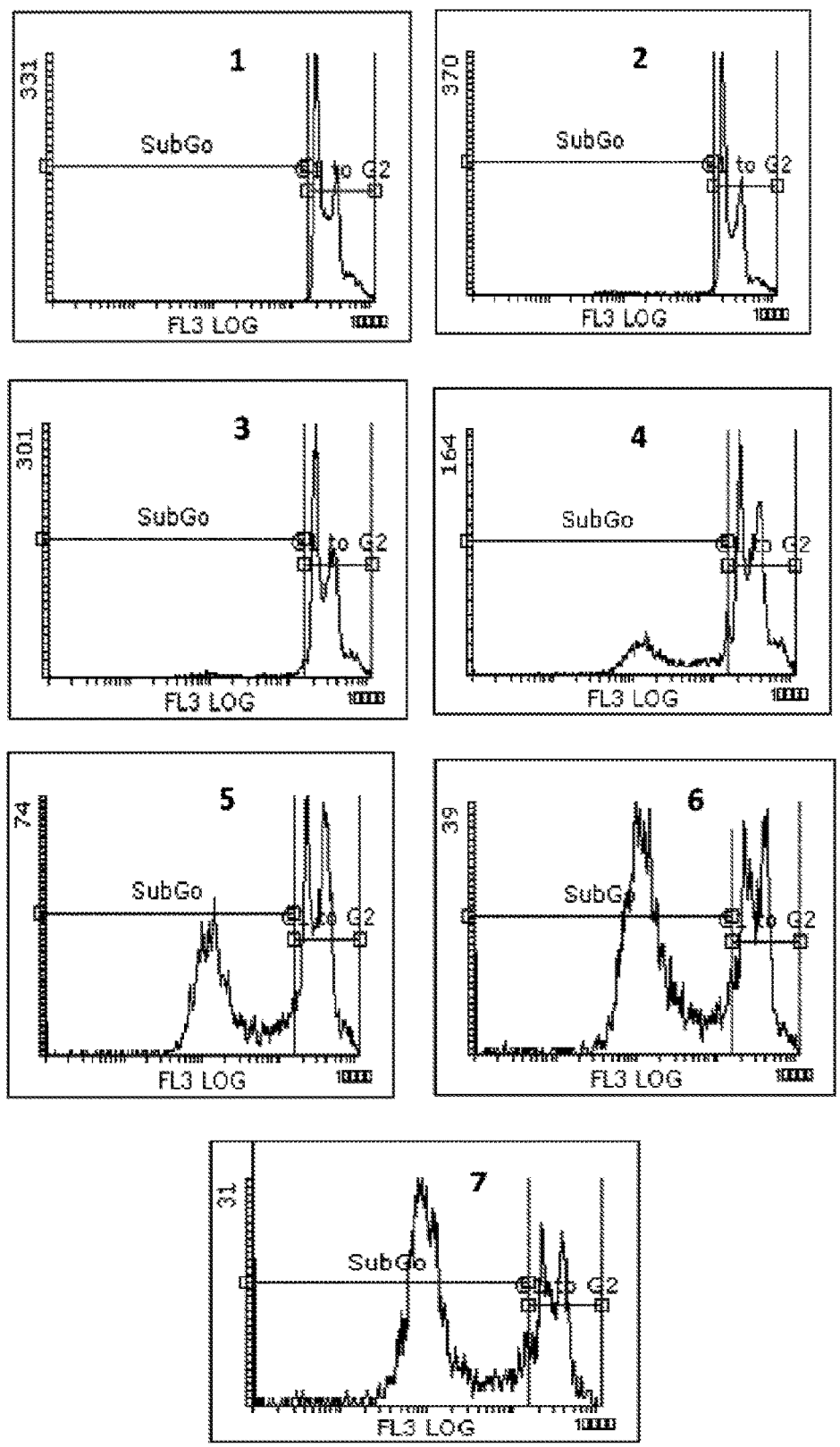

FIG. 18: Graphical representation of the changes in the SubG0 peak of the HOS cells treated with SV for 48 hours. 1=control; 2=SV 0.2 µM; 3=SV 0.5 µM; 4=SV 1.0 µM; 5=SV 2.0 µM; 6=SV 5.0 µM; and 7=SV 10 µM. The significant change in the profile of the G1-G2/M region and the appearance of the SubG0 peak at a concentration below SV 0.2 µM (2) with a maximum at an SV concentration of 10 µM, indicative of cell death by apoptosis.

Figure 19:
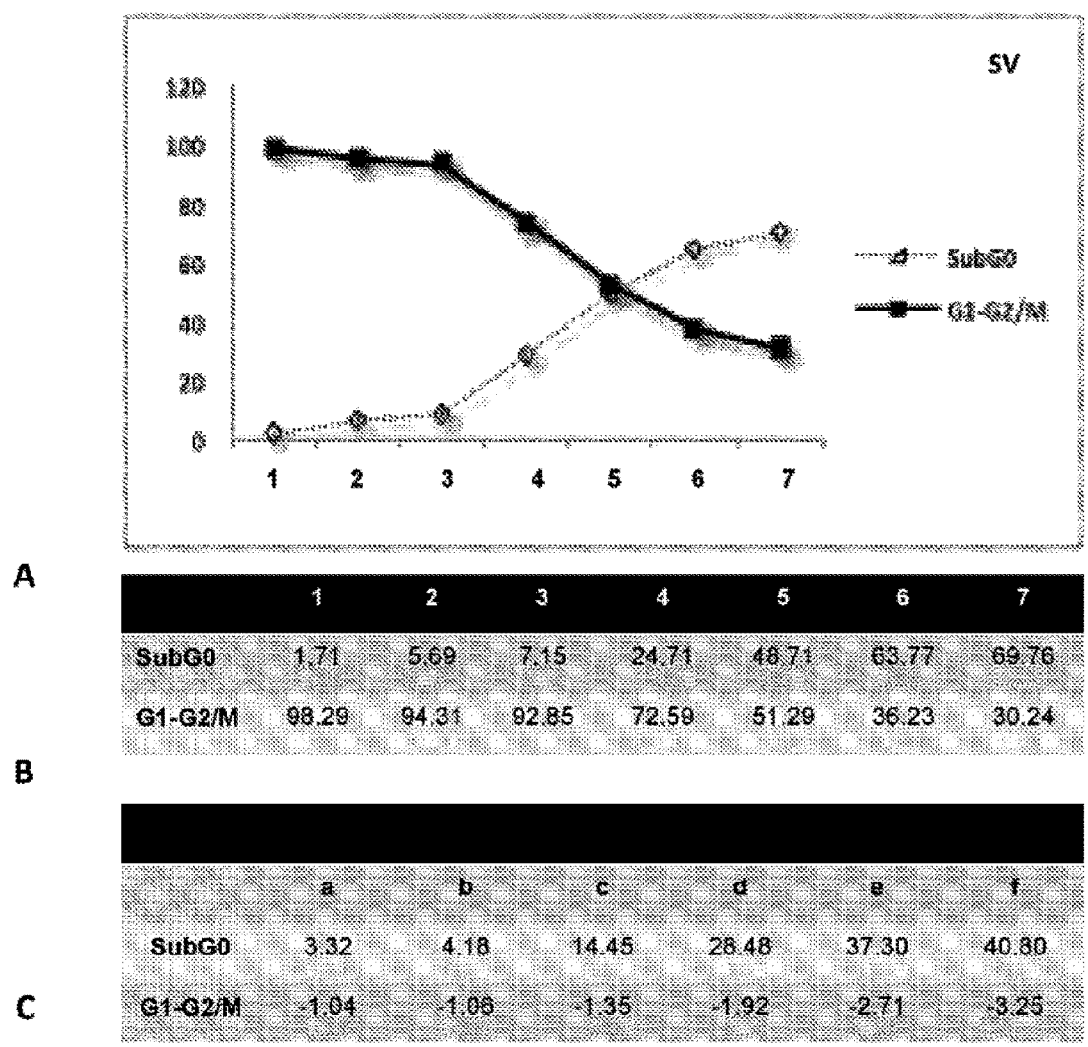

FIG. 19: (A) Graphical representation of the changes in the SubG0 peak and in the G1-G2/M region of the HOS cells treated with increasing doses of SV for 48 hours. The X-axis shows the concentrations of SV: 1=control; 2=0.2 µM; 3=0.5 µM; 4=1.0 µM; 5=2.0 µM; 6=5.0 µM; and 7=10 µM. (B) Absolute values in each of the regions studied at the aforementioned SV concentrations. (C) Increases or decreases in the values obtained for each of the regions studied compared to the control. a=0.2 µM vs. control; b=0.5 µM vs. control; c=1.0 µM vs. control; d=2.0 µM vs. control; e=5.0 µM vs. control; and f=10 µM vs. control. There is a notable increase in the number of cells quantified in the SubG0 phase at doses above 0.2 µM SV.

Figure 20:
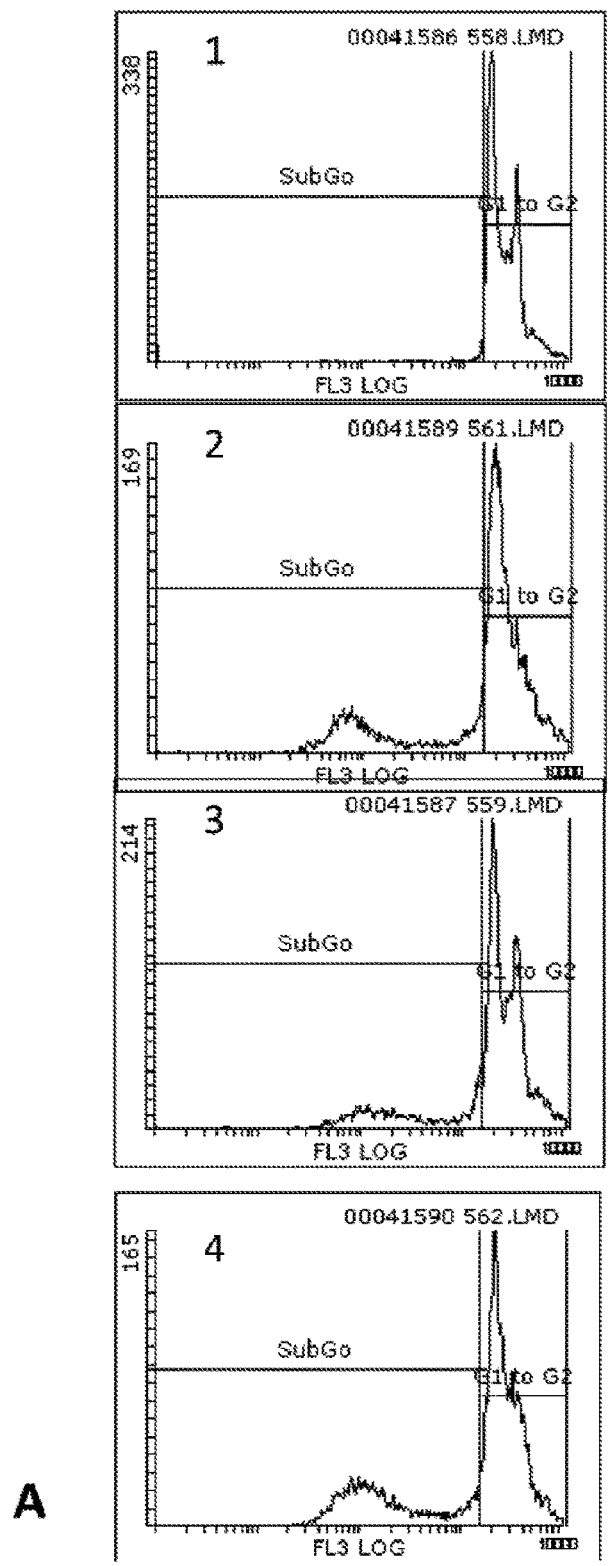

FIG. 20: (A) Representation of the histograms for the changes in the SubG0 peak and in the G1-G2/M region of the HOS cells treated with a combination of SV and MTX for 48 hours. 1=control; 2=MTX 30 nM; 3=SV 0.5 µM; 4=MTX 30 nM+SV 0.5 µM.

Figure 21:
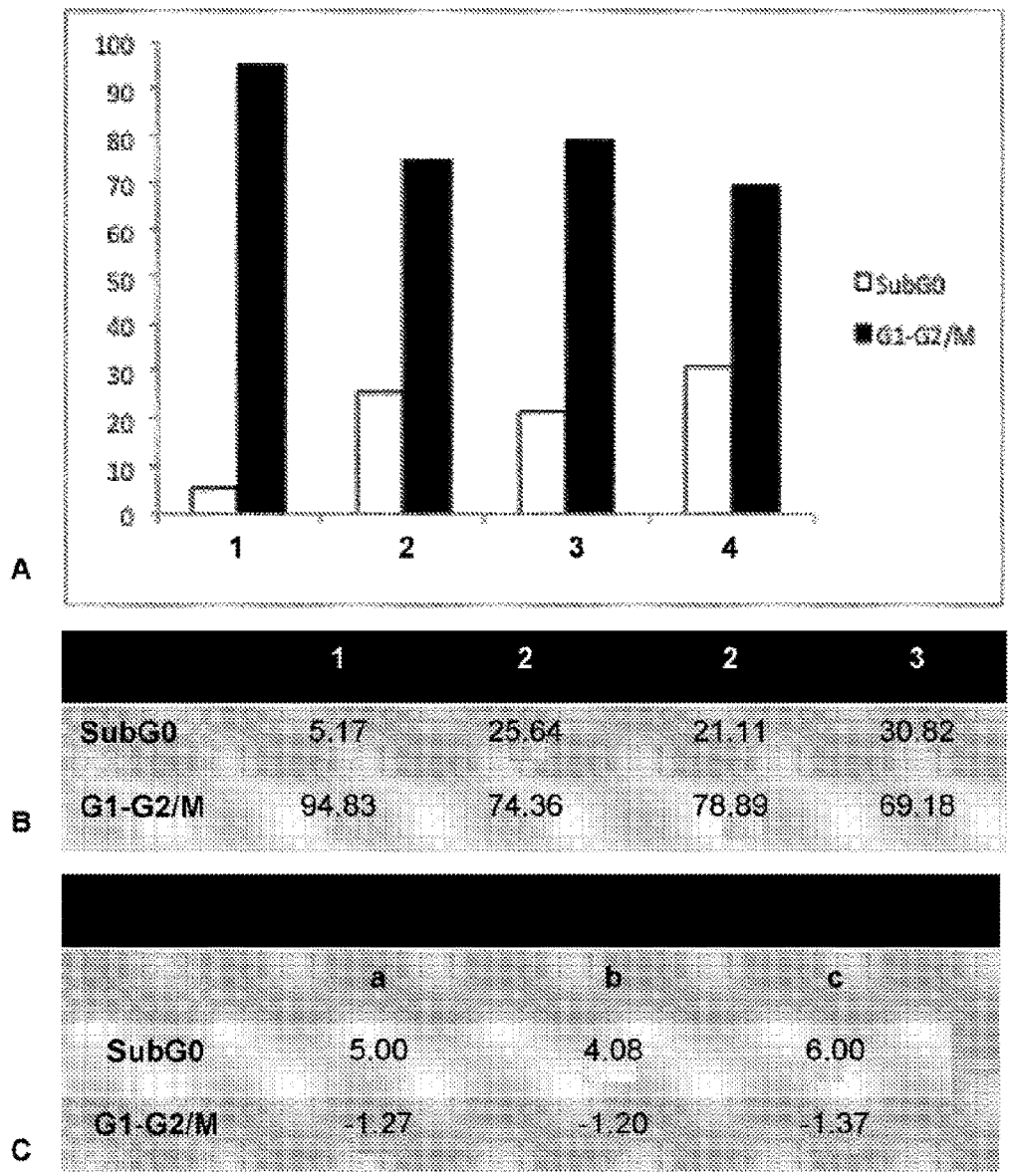

FIG. 21: (A) Graphical representation of the changes in the SubG0 peak and in the G1-G2/M region of the HOS cells treated with a combination of SV and MTX for 48 hours. The X-axis shows the concentrations of the drugs: 1=control; 2=MTX 30 nM; 3=SV 0.5 µM; 4=MTX 30 nM+SV 0.5 µM; (B) Absolute values in the SubG0 peak and in the G1-G2/M region at the aforementioned concentrations. (C) Increases or decreases in the values obtained for each of the regions studied compared to the control. a=MTX 30 nM vs. control; b=SV 0.5 µM vs. control; c=both vs. control. There is a notable increase of up to 6 times in the number of cells in the SubG0 peak (cellular death) when both treatments are combined.

Figure 22:
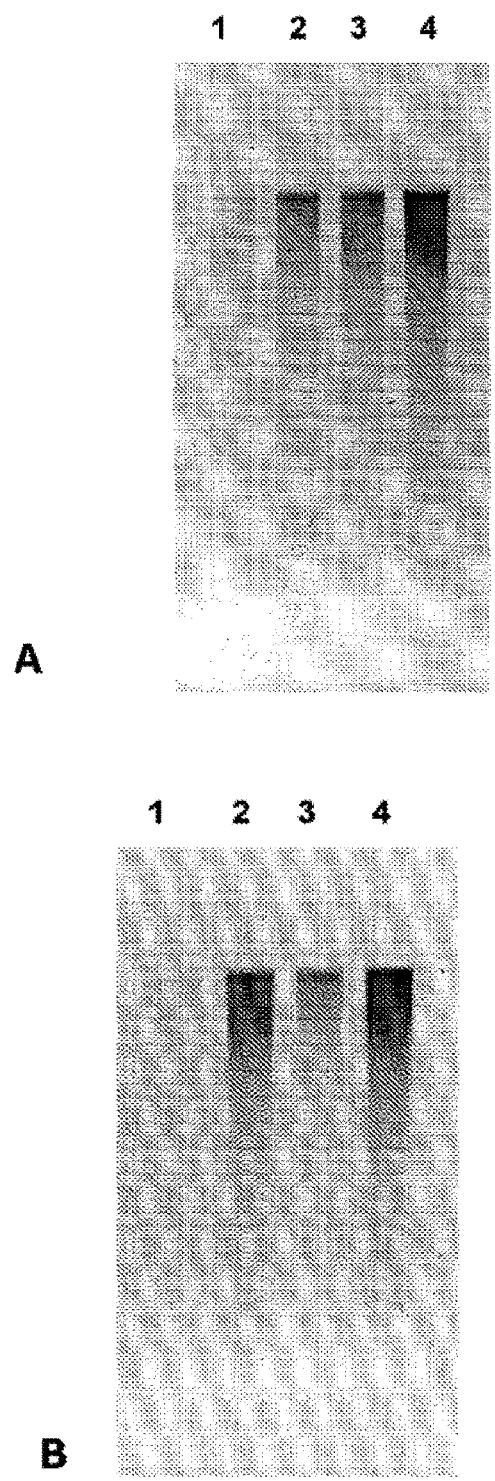

FIG. 22: Graphical representation of the changes in cellular apoptosis of the HOS cells after 24 hours (A) and 36 hours (B) using the DNA ladder technique. 1=control; 2=SV 0.5 µM; 3=MTX 50 nM; 4=MTX 50 nM+SV 0.5 µM.

EXAMPLES

The following examples are provided to better illustrate the claimed invention and they should not be interpreted as limiting the scope of the invention. To the extent that specific materials are mentioned, this is purely for the purposes of illustration and this is not intended to be limiting of the invention. An expert in the technique could develop equivalent measures or reagents without exercising inventive ability and without departing from the scope of the invention.

Example 1

Cultivation of Osteosarcoma Cell Lines

Rat osteosarcoma cell line UMR-106 and human osteosarcoma cell line HOS are cultivated on the RPMI 1640 medium. The human osteosarcoma cell line MG-63 is cultivated on the DMEN medium. All the cultivation media are supplemented with FBS at 10%, 2 mM glutamine, 100 units/ml penicillin and 100 µg/mL streptomycin. The maintenance conditions used for all the cell lines are 37° C. in an atmosphere humidified with 5% $CO_2$. The tumour lines are obtained from the ATCC (American Type Culture Collection) and cultivated according to the recommended conditions.

Example 2

Testing of Cell Survival

The osteosarcoma cell line is cultivated with doses of MTX at 10, 20, 30, 40, 50, 60, 80, and 100 nM and with simvastatin at 0.5 μM and 1.0 μM. Cellular survival is quantified using the sulforhodamine B (SRB) assay, which is a non-radioactive colorimetric test for spectrophotometric quantification based on the electrostatic bonding of the SRB to basic amino acids fixed with trichloroacetic acid (TCA).

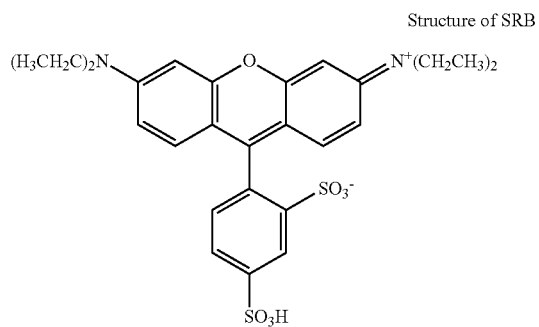

Structure of SRB

For this, the UMR-106, HOS and MG-63 tumour cell lines are cultivated at a density of $5 \times 10^3$ cells/well in 200 μL of culture medium supplemented with 10% FBS on plates of ninety six wells and grown for 24, 48 or 72 hours. Once the experiment is finished the media is removed by decanting. After adding 50 μL/well of TCA 10% (100 mL TCA 100% (w/v)+900 mL Elix $H_2O$, 2-5° C.) cold, the cells are incubated for 30 minutes at 4° C. to completely fix the cells to the base of the well. The TCA is then removed by decanting and the well gently washed with running cold water at least 4 times, ensuring that all the wells are washed equally. The plates are then inverted and placed face down on several layers of adsorbent paper until the next day, ensuring the elimination of almost all the water. Next, 40 μL of sulforhodamine B solution (Sigma S-9012, 4 gr SRB+1 L acetic acid (vol/vol), at ambient temperature) is added to 0.4% (wt/vol) in 1% (vol/vol) acetic acid, avoiding doing so in direct light (SRB is photosensitive). The plates are incubated at ambient temperature for 30 minutes. The dye is then decanted and the wells washed at least 4 times with acetic acid at 1% (vol/vol, 100 mL acetic+10 L Elix $H_2O$), ensuring that all traces of the dye are removed that are not bound with the cells. All the remaining acetic acid is then removed by firmly shaking the plates against a number of layers of absorbent paper overnight in darkness. Next, 150 μL of TRIS:BASE 10 mM (pH 10.5, 100 mL TRIS:BASE 100 mM+900 mL of Hellix $H_2O$) is added and left for 10 minutes at ambient temperature to ensure the complete dissolution of the dye. Lastly, the measurements are taken using the multi-plate Dual Reader at 492 nm (peak absorbance of SRB) and at 620 nm (to remove possible interference caused by small variations in volume, dirt or imperfections in the plate. Before the measurement it is necessary to shake the plates rapidly.

The results of the cellular survival tests are provided in FIGS. 1-5. The results show that the simvastatin significantly reduces the effective dosage of MTX when they are co-administered. This effect is especially relevant at low concentrations of MTX, between 0 nM and 30 nM MTX.

Example 3

Cell Viability Test

The HOS cells are cultivated in a culture medium supplemented with 5-10% heat-inactivated foetal bovine serum and 2 mM of L-glutamine, at 37° C., 95% humidity and 5% atmospheric $CO_2$. The cells are treated with 0.5 μM of simvastatin and with 50 nM of MTX for 24, 48 and 72 hours. The cells are collected by trypsinization. This involves first aspirating the cultivation medium; the cells are then washed with 2-3 mL of PBS (sterile); add 0.5-1 mL of trypsin-EDTA solution (sterile); incubated at 37° for 5 minutes; the cells are collected with 5 mL of fresh culture medium; and the suspension is placed in a sterile 15 mL tube. The trypan blue dye is used in order to determine cell viability. Trypan blue is a colloid that enters the cells through breaks in the cell membrane. Therefore, the cells that appear in the image, clearly stained blue, are considered to be non-viable. For the measurement, mix 50 μL of the trypan blue solution and 50 μL of cell suspension are placed in a 1.5 mL tube. The mixture is homogenised and 10 μL placed in a Neubauer chamber. The total cells and the non-viable cells (completely stained blue) are counted.

The results of the cell viability testing can be seen in FIGS. 6, 7, 8, 9 and 10.

From these experiments it is possible to conclude that the simvastatin has a predominant effect on the induction of cell death; that the methotrexate preferentially acts to slow cell proliferation; and that when both treatments are applied the proliferation is slowed to a greater extent and cell death is increased more than when both treatments are administered separately.

Example 4

Detection of Apoptosis

The detection and quantification of apoptosis is undertaken through the testing of DNA fragmentation and through flow cytometry with Annexin-V/PI staining.

4.1 Test for DNA Fragmentation (Ladder DNA). The UMR-106 tumour cell line is cultivated at a density of $2 \times 10^5$ cells/well on plates with 6 wells for two or three days. Next, the cell culture is incubated with simvastatin at 0.5 μM and MTX 50 nM for 24 and 48 hours. After obtaining the cells in each experimental condition in micro-centrifuge tubes, the cells are lysed in 200 μL of a buffer containing Tris/HCl 10 mM pH 8.0, EDTA 1 mM, Triton X-100 0.2% and centrifuged at 12,000×g for twenty minutes in a Biofuge Stratos micro-centrifuge, Heraeus Instruments. The samples are incubated with RNase (Sigma) to eliminate its RNA content, at a final concentration of 5 mg/mL for one hour at 37° C. and with proteinase K (Sigma) (20 mg/mL) for one hour at 37° C. After a number of washings whose principle component is phenol, the samples are precipitated with 2 volumes of absolute ethanol at −20° C. for at least 12 hours. The samples are then centrifuged again at 12,000×g and the experimental conditions are washed with 70% ethanol in order to add 50 μL of TE Buffer containing Tris/HCl 10 mM pH 8.0, EDTA 1 mM pH 8.0. The samples are analysed on a 1% agarose gel. The DNA content of 123 bp is stained with ethidium bromide and visualised using a UV light system (Bio Imaging System-Syngene). The densitometric analysis is undertaken using the Scion Image Beta 4.02 for Windows public domain software.

The DNA fragmentation test results are shown in FIG. 22. Note the boosting of the apoptotic response when the cells are treated with SV and MTX.

4.2 Flow Cytometry with Annexin-V/PI. An AnnexinV-FITC Apoptosis Detection Kit (Ref: 556547, Becton Dickinson, Pharmingen™) is used to detect and quantify the cells under apoptotic conditions. The cells are seeded on plates with 6 wells for three days. They are then treated with simvastatin at 0.5 µM and MTX 50 nM for 24 and 48 hours. They are then incubated with 100 µL of binding buffer containing 4 µL Annexin conjugated with fluorescein isothiocyanate (AnnexinV-FITC) and 10 µL propidium iodide for fifteen minutes in the dark and at ambient temperature. The cells are then resuspended in 400 µL of the same binding buffer and kept in the dark. The solution is analysed using FACSCalibur flow cytometry (Becton Dickinson, San Jose, Calif.) and the histograms quantified using the Cell Quest software (Becton Dickinson). Under these conditions and in order to distinguish apoptotic processes from necrotic processes and to discount cellular viability, each of the results is calculated using the following formula:

% cells=Annexin V-FITC+*PI*−/*PI*−

Where PI− is the sum of the cells that are considered to be viable (Annexin V-FITC−PI−) and the cells that are found in an apoptotic state (Annexin V-FITC+PI−).

The results of the apoptosis testing using flow cytometry are shown in FIGS. 16-22. The results indicate that the combination of the two drugs induces greater cell death than when they are administered separately.

5. Analysis of the Cell Cycle

In order to analyse the changes in the distribution of the cell cycle the cells are seeded and treated under the same conditions employed with the Annexin V dye. The treated and untreated cells are resuspended in NP-40 at 1% dissolved in PBS additionally containing 50 µg/mL PI at a density of $3\times10^5$ cells/sample. The analysis and quantification of each of the experimental conditions is then carried out after 15 minutes incubation in the dark and at ambient temperature, following the same methodology as employed in the apoptosis experiments with Annexin-V staining (FACSCalibur flow cytometry and Cell Quest software).

The results of the studies into the changes in the distribution of the cell cycle are provided in FIGS. 11-15. The results indicate that MTX essentially provokes a halt in the cycle in phase G1; that SV halts the cycle in phase G2/M; and that the combination of the two halts the cycle in both phases with a significant decrease in the synthesis of DNA, the combination therefore prevents the cell from escaping control over the cell cycle.

The invention claimed is:

1. Method for the treatment or the prevention of osteosarcoma in a subject that requires it, wherein treatment or prevention comprises administering simultaneously, separately or sequentially to said subject:
   a) a quantity of an inhibitor of the dihydrofolate reductase enzyme selected from the group that consists of methotrexate, and a pharmaceutically acceptable salt thereof, comprising between 12 to 15 mg/m$^2$ of body surface area; and
   b) a quantity of a lipophilic statin comprising between 20 to 80 mg/m$^2$ of body surface area, wherein the lipophilic statin is simvastatin.

2. Method according to claim 1, wherein the inhibitor of the dihydrofolate reductase enzyme (a) is administered simultaneously with the lipophilic statin (b).

3. Method according to claim 1, wherein the inhibitor of the dihydrofolate reductase enzyme (a) and the lipophilic statin (b) are administered separately, in any order.

4. Method according to claim 1, wherein the inhibitor of the dihydrofolate reductase enzyme is administered with a frequency comprised between 1 and 5weeks and the lipophilic statin is administered with a frequency comprised between 1 and 7days.

* * * * *